(12) United States Patent
Vogelstein et al.

(10) Patent No.: US 6,255,464 B1
(45) Date of Patent: Jul. 3, 2001

(54) MAD-RELATED GENES IN THE HUMAN

(75) Inventors: Bert Vogelstein, Baltimore; Kenneth W. Kinzler, Belair, both of MD (US); Gregory R. Riggins, Durham, NC (US); Sam Thiagalingam, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/840,767

(22) Filed: Apr. 16, 1997

Related U.S. Application Data

(60) Provisional application No. 60/015,823, filed on Apr. 18, 1996.

(51) Int. Cl.$^7$ .......................... C07H 21/02; C07H 21/04; C07K 1/00
(52) U.S. Cl. .................. 536/23.1; 536/23.5; 530/350
(58) Field of Search ................................ 536/23.1, 23.5; 530/350

(56) References Cited

U.S. PATENT DOCUMENTS

| | | | |
|---|---|---|---|
| 5,834,248 | * | 11/1998 | Falb ..................................... 435/70.1 |
| 5,866,693 | * | 2/1999 | Laping ................................. 536/23.1 |
| 6,017,755 | * | 1/2000 | Wrana et al. ....................... 435/320.1 |

OTHER PUBLICATIONS

Eppert, K. et al., Cell, vol. 86, pp. 543–552, Aug. 23, 1996.*
Yingling, J. et al., Proc. Natl. Acad. Sci. USA, vol. 93, pp. 8940–8944, Aug. 23, 1996.*
Riggins, G. et al., Nature Gen., vol. 13, pp. 347–349, Jul. 1996.*
Nishimura, R. et al., Genbank, Accession No. U73825, Feb. 4, 1997.*
Hoodless, P. et al., Genbank, Accession No. U54826, May 25, 1996.*
Zhang et al., "The tumor suppressor Smad4/DPC 4 as a central mediator of Smad function" Current Biology, Mar. 19, 1997, vol. 7, No. 4, pp. 270–276.
Zhang et al., "Receptor–associated Mad homologs synergize as effectors of the TGF–beta response" Nature, Sep. 12, 1996, vol. 383, pp. 168–172.
Lagna et al., "Partnership between DPC4 and SMAD proteins in TGF–beta signalling pathways" Nature, Oct. 31, 1996, vol. 383, pp. 832–836.
Graff et al., "Xenopus Mad proteins transduce distinct subsets of signals for the TGF beta superfamily", Cell May 17, 1996, vol. 86, pp. 479–487.
Nakao et al., "Identification of Smad2, a human mad–related protein in the transforming growth factor beta signaling pathway" Journal of Biology Chemistry, Jan. 31, 1997, vol. 272, No. 5, pp. 2896–2900.
Derynck et al., "Nomenclature: vertebrate mediators of TGF beta family signals" Cell, Oct. 18, 1996, vol. 87, p. 173.

* cited by examiner

*Primary Examiner*—Ponnathapu Achutamurthy
*Assistant Examiner*—Peter P. Tung
(74) *Attorney, Agent, or Firm*—Banner & Witcoff, LTD

(57) ABSTRACT

Five human genes related to the Mad gene of Drosophila were identified. One of these genes (Smad2) was found to reside at chromosome 18q21, adjacent to a previously described member of this family called DPC4 (Smad4). Smad2 was found to be somatically mutated in two of eighteen human colorectal cancers. Smad2 and Smad4 are important in the suppression of neoplasia by mediating the growth inhibitory effects of TGF-β-like ligands.

3 Claims, 8 Drawing Sheets

FIG. 1

```
MAD     TKMCTIRMSFVKGWGAEYHRQDVTSTPCWIEIHLHGPLQWLDKVLTQMgsphnaisSMS-
SMA4    RDFCTIAISFVKAWGDVYQRKTIKETPCWIEVTLHRPLQILDQLLKNSsqfgss-----
SMA3    SKHCFIRISFVKGWGEDYPRQDVTSTPCWLELRLNVPLAYIDQKMKQTprtnlmepNSM
SMA2    QKMTFIRMSFVKGWGAEYQRQDVTSTPCWIEIHLHAPLAWLDRVLSTMgptprpisSIS-
DPC4    RRLCILRMSFVKGWGPDYPRQSIKETPCWIEIHLHRALQLLDEVLHTMpiadpqpld--
SMAD2   TRMCTIRMSFVKGWGAEYRRQTVTSTPCWIELHLNGPLQWLDKVLTQMgspsvrcsSMS-
SMAD1   TKMCTIRMSFVKGWGAEYHRQDVTSTPCWIEIHLHGPLQWLDKVLTQMgsphnpisSMS-
SMAD6   ydpnSVRISFAKGWGPCYSRQFITSCPCWLEILLNNPr---------------------
SMAD3   TRMCTIRMSFVKGWGAEYRRQTVTSTPCWIELHLNGPLQWLDKVLTQMgspsircsSMS-
```

FIG. 2

| | |
|---|---|
| SMAD2 | ----------------------------MSSILPFTPPVVKRLLGWKksaggsgggaggeqNGQEEKWCEKAVKSLVKKLKKTGRLDELEK 63 |
| MAD | mdtddvesntssamstLGSLFSFTSPAVKKLLGWKQ-------GDEEEKWAEKAVDSLVKKLKKRGALEEELER 67 |
| SMAD2 | ATTTQNCNTKCVTIPstcseiwglstpntidqwdttglysfseqtRSLDGRLQVSHRKGLPHVIYCRLWRWPDLHSHHEL 143 |
| MAD | ALSCPGQPSKCVTIP--------------------------------RSLDGRLQVSHRKGLPHVIYCRWRWPDLQSHHEL 117 |
| SMAD2 | KAIENCEYAFNLKKDEVCVNPYHYQRVETPVLPPVLVPRHTEil tel pp[]ddythsipentnfpagiepqsnyiPETPPP 223 |
| MAD | KPLELCQYPFSAKDKEVCINPYHYKRVESPVLPPVLPPVLVPRHSEFapghsml]qfnhvae--------PSMPHN 180 |
| SMAD2 | GYISEDGETSPDQLNQSMDTGSPAELSPTTLSPVNHSLDLQPVTYS---------------------EPAF 273 |
| MAD | VSYSNSGFNSHSLSTSNTSVGSPDSSVNSNPNSPYDSLAGTPPPAYSpsedgnsnnpndgqqlldaqmgdvaqvsysEPAF 260 |
| SMAD2 | WCSTAYYELNQRVGETFHASQPSLTVDGFTDPSNSERFCLGLLSNVNRNATVEMTRRHIGRGVRLYYIGGEVFAECLSD 352 |
| MAD | WASTAYYELNCRVGEVFHCNNNSVWDGFTDPSMNSDRCCLGQLSNVNRNSTIENTRRHIGKGVHLYYVTGEVYAECLSD 340 |
| SMAD2 | SAIFVQSPNCNQRYGWHPATVCKIPPGCNLKIFNNQEFAALLAQSVNQGFEAVYQLTRMCTIRMSFVKGWGAEYRRQTVT 432 |
| MAD | SAIFVQSRNCNYHHGFHPSTVCKIPPGCSLKIFNNQEFAQLLSQSVNGGFEAVYELTKMCTIRMSFVKGWGAEYHRQDVT 420 |
| SMAD2 | STPCWIELHLNGPLQWLDKVLTQMGSPSVRCSSMS 467 |
| MAD | STPCWIEIHLHGPLQWLDKVLTQMGSPHNAISSMS 455 |

FIG. 3A
1 2 3 4
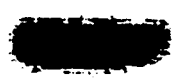 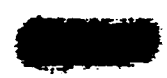     JV18-1
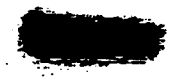    JV15-1

```
339    Tyr Tyr Ile Gly Gly Glu Val Phe Ala Glu Cys Leu Ser Asp Ser Ala Ile Phe Val Gln Ser Pro Asn Cys Asn    363
1114   TAC TAC ATA GGT GGG GAA GTT TTT GCT GAG TGC CTA AGT GAT AGT GCA ATC TTT GTG CAG AGC CCC AAT TGT AAT   1188

1114   TAC TAC ATA GGT GGG GAG AGC CCC AAT TGT AAT   1188
339    Tyr Tyr Ile Gly Gly Glu Ser Pro Asn Cys Asn    363
```

FIG. 4

```
Mad     MDtddvestssaMSTLGSLFSFTSPAVKKLLGWKQGDEEEKWAEKAVDSVKKLKKRKGAIEELERALSCPGQPSKCVTI      81
Smad 5  ------------MTSMASLESFTSPAVKRLLGWKQGDEEEKWAEKAVDALVKKLKKKKGAWEELEKALSPGQPSKCVTI        68
Smad 6  ------------M-----------------------------------------------------------------         1

Mad     PRSLDGRLQVSHRKGLPHVIYCRWRWPDLqshhe kpIeIcqypfsakqkevCINPYHYKRVESPVLPPYVLPPRHSEFAP      162
Smad 5  PRSLDGRLQVSHRKGLPHVIYCRWRWPDLqshhe kpldicefpfgskqkefsCINPYHYKRVESPVLPPYVLPPRHNEFNP      149
Smad 6  ------------------------------------------------------------------------------         1

Mad     GHSMLpfnhvaepsmphnvsysnsgfnshsIstsntsvgsp---------SSVNSNPNSPYDSLAGTPPPAYSPSE          229
Smad 5  QHSLLvqfrnIshneptmpqnatfpdsfipqpnnapfpIspnspyppspasstypnSPASSGPGSPFQLPADTPPPAYMPPD    230
Smad 6  ----------------------------------------------------SRMGKPIETQK-SPPPPYSRLS             22

Mad     Dgnsmmpndqgql1daqmg----------SEPAFWASIAYYELNCRVGEVFHCNNNSTVNDGFTNPSN                  294
Smad 5  DqmapdnsqpmdtssnmipqtmpsissrDVQPVAY-------EEPKHWCSIVYYELNNRVGEAFHASSTSVLMDGFTDPSN    304
Smad 6  PrdeykpIqh sdstIsyteteatnslitapgefsdasmspdaTKDSHWCSVAYWEHRTRVGRLYAVYDQAVSIfydlpqg-     102

Mad     NSDRCCLGQLGSNVNRNSTIENTRRHTGKGVHLIYYTGEVYAECLSDSAIFVQSPNCNYHGFPSTVCKIPPGCSLKIFNN      375
Smad 5  NKSRFCLGLLSNVNRNSTIENTRRHIGKGVHLIYYVGGEVYAECLSDSSIFVQSPNCNFHGFPTTVCKIPSSCSLKIFNN      385
Smad 6  --SGFCLGQLNLEQRSFSVPRTRDSKLGFGIILLSKEPDGVWAYNRGEHPLEVNSpt1dap--GGRALVWRKVPPGYSLKVEDf   180

Mad     QEFAQLLSQSVWNGFEAVYELTKMCTIRMSFVKGWGAEYHRQDVTSTPCWIEIHLHGPLQWLDKVLTQMGSPHNATSSVS      456
Smad 5  QEFAQLLAQSVWNGFEAVYELTKMCTIRMSFVKGWGAEYHRQDVTSTPCWIEIHLHGPLQWLDKVLTQMGSPLNPISSVS      465
Smad 6  ersqIqhapepdaaIgpydpn-----SYRISFAKGWGPCYSRQFITSCPCWLEILLNNpr                          236
```

FIG. 5

| GENE | LOCATION | DH1a | DH1b | DH2a | DH2b | TOTAL AA | HUMAN ACC. # | MOUSE ACC. # |
|------|----------|------|------|------|------|----------|--------------|--------------|
| Smad1 | 4q28-31 | | | | | 465 | U59912 | U74359 |
| Smad2 | 18q21 | | | | | 467 | U59911 | U60530 |
| Smad3 | 15q21-22 | | | | | 425 | U76622 | AA023642 |
| Smad4 | 18q21 | | | | | 552 | U44378 | W41362 |
| Smad5 | 5q31 | | | | | 465 | U59913 | U58993 |
| Smad6 | 15q21-22 | | | | | 235 | U59914 | W41111 |

FIG. 6
A
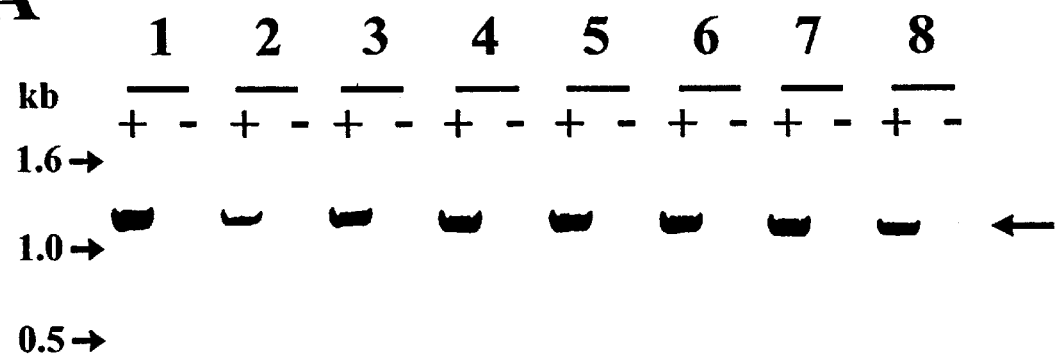
B
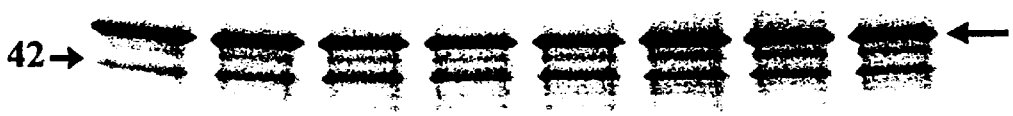

SEQUENCE LISTING

<160> NUMBER OF SEQ ID NOS: 53

<210> SEQ ID NO 1
<211> LENGTH: 1992
<212> TYPE: DNA
<213> ORGANISM: Homo sapiens

<400> SEQUENCE: 1

| | | | | | |
|---|---|---|---|---|---|
| catactacgt | gggcggagaa | gcagctcgcc | agccagcagc | ccgccagccg | ccgggaggtt | 60 |
| cgatacaaga | ggctgttttc | ctagcgtggc | ttgctgcctt | tggtaagaac | atgtcgtcca | 120 |
| tcttgccatt | cacgccgcca | gttgtgaaga | gactgctggg | atggaagaag | tcagctggtg | 180 |
| ggtctggagg | agcaggcgga | ggagagcaga | atgggcagga | agaaaagtgg | tgtgagaaag | 240 |
| cagtgaaaag | tctggtgaag | aagctaaaga | aaacaggacg | attagatgag | cttgagaaag | 300 |
| ccatcaccac | tcaaaactgt | aatactaaat | gtgttaccat | accaagcact | tgctctgaaa | 360 |
| tttgggact | gagtacacca | aatacgatag | atcagtggga | tacaacaggc | ctttacagct | 420 |
| tctctgaaca | aaccaggtct | cttgatggtc | gtctccaggt | atcccatcga | aaggattgc | 480 |
| cacatgttat | atattgccga | ttatggcgct | ggcctgatct | tcacagtcat | catgaactca | 540 |
| aggcaattga | aaactgcgaa | tatgcttta | atcttaaaaa | ggatgaagta | tgtgtaaacc | 600 |
| cttaccacta | tcagagagtt | gagacaccag | ttttgcctcc | agtattagtg | ccccgacaca | 660 |
| ccgagatcct | aacagaactt | ccgcctctgg | atgactatac | tcactccatt | ccagaaaaca | 720 |
| ctaacttccc | agcaggaatt | gagccacaga | gtaattatat | tccagaaacg | ccacctcctg | 780 |
| gatatatcag | tgaagatgga | gaaacaagtg | accaacagtt | gaatcaaagt | atggacacag | 840 |
| gctctccagc | agaactatct | cctactactc | tttcccctgt | taatcatagc | ttggatttac | 900 |
| agccagttac | ttactcagaa | cctgcatttt | ggtgttcgat | agcatattat | gaattaaatc | 960 |
| agagggttgg | agaaaccttc | catgcatcac | agccctcact | cactgtagat | ggctttacag | 1020 |
| acccatcaaa | ttcagagagg | ttctgcttag | gtttactctc | caatgttaac | cgaaatgcca | 1080 |
| cggtagaaat | gacaagaagg | catataggaa | gaggagtgcg | cttatactac | ataggtgggg | 1140 |
| aagtttttgc | tgagtgccta | agtgatagtc | caatctttgt | gcagagcccc | aattgtaatc | 1200 |
| agagatatgg | ctggcaccct | gcaacagtgt | gtaaaattcc | accaggctgt | aatctgaaga | 1260 |
| tcttcaacaa | ccaggaattt | gctgctcttc | tggctcagtc | tgttaatcag | ggttttgaag | 1320 |
| ccgtctatca | gctaactaga | atgtgcacca | taagaatgag | ttttgtgaaa | gggtggggag | 1380 |
| cagaataccg | aagcagacg | gtaacaagta | ctccttgctg | gattgaactt | catctgaatg | 1440 |
| gacctctaca | gtggttggac | aaagtattaa | ctcagatggg | atccccttca | gtgcgttgct | 1500 |
| caagcatgtc | ataaagcttc | accaatcaag | tcccatggaa | aagacttaat | gtaaacaact | 1560 |
| ctctctcggt | caatagcatt | ggtgttgtgg | tcccctatg | ggactgttta | cctattccaa | 1620 |
| aaggtttcaa | ggagagaaaa | ccagcacttg | aggtcctcat | ccaattaaag | cacccttgtg | 1680 |
| gaatcctgtt | tccctatatt | tgaatattag | gatgggaaaa | ttagtgtcta | gaaatactct | 1740 |
| ccccattaaa | gaggaagaga | agattttaaa | gacttaatga | tgtcttattg | ggcataaact | 1800 |
| gagtgtccca | aaggtttatt | aataacagta | gtagttatgt | gtacaggtaa | tgtatcatga | 1860 |
| tccagtatca | cagtattgtg | ctgtttatat | acatttttag | tttgcataga | tgaggtgtgt | 1920 |
| gtgtgcgctg | cttcttgatc | taggcaaacc | tttataaagt | tgcagtacct | aaaaaaaaaa | 1980 |
| aaaaaaaaaa | aa | | | | | 1992 |

<210> SEQ ID NO 2
<211> LENGTH: 477
<212> TYPE: PRT
<213> ORGANISM: Homo sapiens

<400> SEQUENCE: 2

```
Val Ala Met Ile Asn Ala Cys Ile Asp Ser Met Ser Ser Ile Leu Pro
  1               5                  10                  15

Phe Thr Pro Pro Val Val Lys Arg Leu Leu Gly Trp Lys Lys Ser Ala
                 20                  25                  30

Gly Gly Ser Gly Gly Ala Gly Gly Glu Gln Asn Gly Gln Glu Glu
             35                  40                  45

Lys Trp Cys Glu Lys Ala Val Lys Ser Leu Val Lys Lys Leu Lys Lys
 50                  55                  60

Thr Gly Arg Leu Asp Glu Leu Glu Lys Ala Ile Thr Thr Gln Asn Cys
 65                  70                  75                  80

Asn Thr Lys Cys Val Thr Ile Pro Ser Thr Cys Ser Glu Ile Trp Gly
                 85                  90                  95

Leu Ser Thr Pro Asn Thr Ile Asp Gln Trp Asp Thr Thr Gly Leu Tyr
                100                 105                 110

Ser Phe Ser Glu Gln Thr Arg Ser Leu Asp Gly Arg Leu Gln Val Ser
            115                 120                 125

His Arg Lys Gly Leu Pro His Val Ile Tyr Cys Arg Leu Trp Arg Trp
130                 135                 140

Pro Asp Leu His Ser His His Glu Leu Lys Ala Ile Glu Asn Cys Glu
145                 150                 155                 160

Tyr Ala Phe Asn Leu Lys Lys Asp Glu Val Cys Val Asn Pro Tyr His
                165                 170                 175

Tyr Gln Arg Val Glu Thr Pro Val Leu Pro Pro Val Leu Val Pro Arg
            180                 185                 190

His Thr Glu Ile Leu Thr Glu Leu Pro Pro Leu Asp Asp Tyr Thr His
            195                 200                 205

Ser Ile Pro Glu Asn Thr Asn Phe Pro Ala Gly Ile Glu Pro Gln Ser
210                 215                 220

Asn Tyr Ile Pro Glu Thr Pro Pro Pro Gly Tyr Ile Ser Glu Asp Gly
225                 230                 235                 240

Glu Thr Ser Asp Gln Gln Leu Asn Gln Ser Met Asp Thr Gly Ser Pro
                245                 250                 255

Ala Glu Leu Ser Pro Thr Thr Leu Ser Pro Val Asn His Ser Leu Asp
            260                 265                 270

Leu Gln Pro Val Thr Tyr Ser Glu Pro Ala Phe Trp Cys Ser Ile Ala
            275                 280                 285

Tyr Tyr Glu Leu Asn Gln Arg Val Gly Glu Thr Phe His Ala Ser Gln
        290                 295                 300

Pro Ser Leu Thr Val Asp Gly Phe Thr Asp Pro Ser Asn Ser Glu Arg
305                 310                 315                 320

Phe Cys Leu Gly Leu Leu Ser Asn Val Asn Arg Asn Ala Thr Val Glu
                325                 330                 335

Met Thr Arg Arg His Ile Gly Arg Gly Val Arg Leu Tyr Tyr Ile Gly
            340                 345                 350

Gly Glu Val Phe Ala Glu Cys Leu Ser Asp Ser Ala Ile Phe Val Gln
            355                 360                 365

Ser Pro Asn Cys Asn Gln Arg Tyr Gly Trp His Pro Ala Thr Val Cys
```

-continued

```
            370                 375                 380
Lys Ile Pro Pro Gly Cys Asn Leu Lys Ile Phe Asn Asn Gln Glu Phe
385                 390                 395                 400

Ala Ala Leu Leu Ala Gln Ser Val Asn Gln Gly Phe Glu Ala Val Tyr
                405                 410                 415

Gln Leu Thr Arg Met Cys Thr Ile Arg Met Ser Phe Val Lys Gly Trp
            420                 425                 430

Gly Ala Glu Tyr Arg Arg Gln Thr Val Thr Ser Thr Pro Cys Trp Ile
        435                 440                 445

Glu Leu His Leu Asn Gly Pro Leu Gln Trp Leu Asp Lys Val Leu Thr
    450                 455                 460

Gln Met Gly Ser Pro Ser Val Arg Cys Ser Ser Met Ser
465                 470                 475

<210> SEQ ID NO 3
<211> LENGTH: 1524
<212> TYPE: DNA
<213> ORGANISM: Homo sapiens

<400> SEQUENCE: 3
cccccctcat catcatcatc aatcaatcaa tcaattttac ttacctcctc ctctacctct      60
actcagttca gttactcatc atacaataat aattacaatt actcagattc acactacaat     120
gagtctcaat gagtctcaat gagtctcaat gagtctcaat gagtctcaat gagtcagaaa     180
aaaaaaatga tctactacat aggacataat aaactctcat atctcataac acccatacta     240
cgtgaaaaga acgaatccag caccaaaacg tgctacaaca tggatgaact tcgatgactt     300
tgtgccacat gaaagaagaa gccagccaca aaaggccata tattgtatga aatgaaatgt     360
ccagaatggg caaacccata gagacacaaa atctccgcc acctccctac tctcggctgt      420
ctcctcgcga cgagtacaag ccactggatc tgtccgattc acattgtct tacactgaaa      480
cggaggctac caactccctc atcactgctc cgggtgaatt ctcagacgcc agcatgtctc     540
cggacgccac caagccgagc cactggtgca gcgtggcgta ctgggagcac cggacgcgcg     600
tgggccgcct ctatgcggtg tacgaccagg ccgtcagcat cttctacgac ctacctcagg     660
gcagcggctt ctgcctgggc cagctcaacc tggagcagcg cagcgagtcg gtgcggcgaa     720
cgcgcagcaa gatcggcttc ggcatcctgc tcagcaagga gcccgacggc gtgtgggcct     780
acaaccgcgg cgagcacccc atcttcgtca actccccgac gctggacgcg cccggcggcc     840
gcgccctggt cgtgcgcaag gtgccccccg gctactccat caaggtgttc gacttcgagc     900
gctcgggcct gcagcacgcg cccgagcccg acgccgccga cggcccctac gaccccaaca     960
gcgtccgcat cagcttcgcc aagggctggg ggccctgcta ctcccggcag ttcatcacct    1020
cctgcccctg ctggctggag atcctcctca acaaccccag atagtggcgg ccccggcggg    1080
agggcgggt gggaggccgc ggccaccgcc acctgccggc ctcgagaggg gccgatgccc    1140
agagacacag cccccacgga caaaaccccc cagatatcat ctacctagat ttaatataaa    1200
gttttatata ttatatggaa atatatatta tacttgtaat tatggagtca ttttttacaat    1260
gtaattattt atgtatggtg caatgtgtgt atatggacaa aacaagaaag acgcactttg    1320
gcttataatt ctttcaatac agatatattt tctttctctt cctccttcct cttccttact    1380
ttttatatat atatataaag aaaatgatac agcagagcta ggtggaaaag cctgggtttg    1440
gtgtatggtt tttgagatat taatgcccag acaaaaagct aataccagtc actcgataat    1500
aaagtattcg cattataaaa aaga                                           1524
```

<210> SEQ ID NO 4
<211> LENGTH: 246
<212> TYPE: PRT
<213> ORGANISM: Homo sapiens

<400> SEQUENCE: 4

```
Val Phe Ala Met Ile Asn Ala Cys Ile Asp Ser Met Ser Arg Met Gly
 1               5                  10                  15

Lys Pro Ile Glu Thr Gln Lys Ser Pro Pro Pro Tyr Ser Arg Leu
            20                  25                  30

Ser Pro Arg Asp Glu Tyr Lys Pro Leu Asp Leu Ser Asp Ser Thr Leu
            35                  40                  45

Ser Tyr Thr Glu Thr Glu Ala Thr Asn Ser Leu Ile Thr Ala Pro Gly
    50                  55                  60

Glu Phe Ser Asp Ala Ser Met Ser Pro Asp Ala Thr Lys Pro Ser His
 65                  70                  75                  80

Trp Cys Ser Val Ala Tyr Trp Glu His Arg Thr Arg Val Gly Arg Leu
                85                  90                  95

Tyr Ala Val Tyr Asp Gln Ala Val Ser Ile Phe Tyr Asp Leu Pro Gln
                100                 105                 110

Gly Ser Gly Phe Cys Leu Gly Gln Leu Asn Leu Glu Gln Arg Ser Glu
            115                 120                 125

Ser Val Arg Arg Thr Arg Ser Lys Ile Gly Phe Gly Ile Leu Leu Ser
    130                 135                 140

Lys Glu Pro Asp Gly Val Trp Ala Tyr Asn Arg Gly Glu His Pro Ile
145                 150                 155                 160

Phe Val Asn Ser Pro Thr Leu Asp Ala Pro Gly Gly Arg Ala Leu Val
                165                 170                 175

Val Arg Lys Val Pro Pro Gly Tyr Ser Ile Lys Val Phe Asp Phe Glu
                180                 185                 190

Arg Ser Gly Leu Gln His Ala Pro Glu Pro Asp Ala Ala Asp Gly Pro
            195                 200                 205

Tyr Asp Pro Asn Ser Val Arg Ile Ser Phe Ala Lys Gly Trp Gly Pro
    210                 215                 220

Cys Tyr Ser Arg Gln Phe Ile Thr Ser Cys Pro Cys Trp Leu Glu Ile
225                 230                 235                 240

Leu Leu Asn Asn Pro Arg
                245
```

<210> SEQ ID NO 5
<211> LENGTH: 1876
<212> TYPE: DNA
<213> ORGANISM: Homo sapiens

<400> SEQUENCE: 5

```
cccccctcat catcatcatc aatcaatcaa tcaattttac ttacctcctc ctctacctct      60
actcagttca gttactcatc atacaataat aattacaatt actcagattc acactacaat     120
gagtctcaat gagtctcaat gagtctcaat gagtctcaat gagtctcaat gagtcagaaa     180
aaaaaaatga tctactacat aggacataat aaactctcat atctcataac acccatacta     240 cgtgggggc gctcctcgcc gcccgcgcgc cctccccagc catgtcgtcc atcctgcctt      300
tcactccccc gatcgtgaag cgcctgctgg gctggaagaa gggcgagcag aacgggcagg     360
aggagaaatg gtgcgagaag gcggtcaaga gcctggtcaa gaaactcaag aagacggggc     420
```

-continued

```
agctggacga gctggagaag gccatcacca cgcagaacgt caacaccaag tgcatcacca    480
tccccaggtc cctggatggc cggttgcagg tgtcccatcg aagggggctc cctcatgtca    540
tctactgccg cctgtggcga tggccagacc tgcacagcca ccacgagcta cgggccatgg    600
agctgtgtga gttcgccttc aatatgaaga aggacgaggt ctgcgtgaat ccctaccact    660
accagagagt agagacacca gttctacctc ctgtgttggt gccacgccac acagagatcc    720
cggccgagtt cccccactg gacgactaca gccattccat ccccgaaaac actaacttcc     780
ccgcaggcat cgagcccag agcaatattc cagagacccc accccctggc tacctgagtg     840
aagatggaga accagtgac caccagatga accacagcat ggacgcaggt tctccaaacc     900
tatccccgaa tccgatgtcc ccagcacata taacttgga cctgcagcca gttacctact      960
gcgagccggc cttctggtgc tccatctcct actacgagct gaaccagcgc gtcggggaga    1020
cattccacgc ctcgcagcca tccatgactg tggatggctt caccgacccc tccaattcgg    1080
agcgcttctg cctagggctg ctctccaatg tcaacaggaa tgcagcagtg gagctgacac    1140
ggagacacat cggaagaggc gtgcggctct actacatcgg aggggaggtc ttcgcagagt    1200
gcctcagtga cagcgctatt tttgtccagt ctcccaactg taaccagcgc tatggctggc    1260
acccggccac cgtctgcaag atcccaccag gatgcaacct gaagatcttc aacaaccagg    1320
agttcgctgc cctcctggcc cagtcggtca accagggctt tgaggctgtc taccagttga    1380
cccgaatgtg caccatccgc atgagcttcg tcaaaggctg gggagcggag tacaggagac    1440
agactgtgac cagtaccccc tgctggattg agctgcacct gaatgggcct ttgcagtggc    1500
ttgacaaggt cctcacccag atgggctccc caagcatccg ctgttccagt gtgtcttaga    1560
gacatcaagt atggtagggg agggcaggct tggggaaaat ggccatacag gaggtggaga    1620
aaattggaac tctactcaac ccattgttgt caaggaagaa gaaatctttc tccctcaact    1680 gaagggggtgc acccacctgt tttctgaaac acacgagcaa acccagaggt ggatgttatg    1740
aacagctgtg tctgccaaac acatttaccc tttggcccca ctttgaaggg caagaaatgg    1800
cgtctgctct ggtggcttaa gtgagcagaa caggtagtat taccaccacg gcaccctccc    1860
cccagactct tttttt                                                    1876
```

<210> SEQ ID NO 6
<211> LENGTH: 436
<212> TYPE: PRT
<213> ORGANISM: Homo sapiens

<400> SEQUENCE: 6

```
Val Phe Ala Met Ile Asn Ala Cys Ile Asp Ser Met Ser Ser Ile Leu
  1               5                  10                  15

Pro Phe Thr Pro Pro Ile Val Lys Arg Leu Leu Gly Trp Lys Lys Gly
             20                  25                  30

Glu Gln Asn Gly Gln Glu Glu Lys Trp Cys Glu Lys Ala Val Lys Ser
         35                  40                  45

Leu Val Lys Lys Leu Lys Lys Thr Gly Gln Leu Asp Glu Leu Glu Lys
     50                  55                  60

Ala Ile Thr Thr Gln Asn Val Asn Thr Lys Cys Ile Thr Ile Pro Arg
 65                  70                  75                  80

Ser Leu Asp Gly Arg Leu Gln Val Ser His Arg Lys Gly Leu Pro His
                 85                  90                  95

Val Ile Tyr Cys Arg Leu Trp Arg Trp Pro Asp Leu His Ser His His
            100                 105                 110
```

Glu Leu Arg Ala Met Glu Leu Cys Glu Phe Ala Phe Asn Met Lys Lys
        115                 120                 125

Asp Glu Val Cys Val Asn Pro Tyr His Tyr Gln Arg Val Glu Thr Pro
        130                 135                 140

Val Leu Pro Pro Val Leu Val Pro Arg His Thr Glu Ile Pro Ala Glu
145                 150                 155                 160

Phe Pro Pro Leu Asp Asp Tyr Ser His Ser Ile Pro Glu Asn Thr Asn
                165                 170                 175

Phe Pro Ala Gly Ile Glu Pro Gln Ser Asn Ile Pro Glu Thr Pro Pro
            180                 185                 190

Pro Gly Tyr Leu Ser Glu Asp Gly Glu Thr Ser Asp His Gln Met Asn
        195                 200                 205

His Ser Met Asp Ala Gly Ser Pro Asn Leu Ser Pro Asn Pro Met Ser
        210                 215                 220

Pro Ala His Asn Leu Asp Leu Gln Pro Val Thr Tyr Cys Glu Pro
225                 230                 235                 240

Ala Phe Trp Cys Ser Ile Ser Tyr Tyr Glu Leu Asn Gln Arg Val Gly
                245                 250                 255

Glu Thr Phe His Ala Ser Gln Pro Ser Met Thr Val Asp Gly Phe Thr
            260                 265                 270

Asp Pro Ser Asn Ser Glu Arg Phe Cys Leu Gly Leu Leu Ser Asn Val
        275                 280                 285

Asn Arg Asn Ala Ala Val Glu Leu Thr Arg Arg His Ile Gly Arg Gly
290                 295                 300

Val Arg Leu Tyr Tyr Ile Gly Gly Glu Val Phe Ala Glu Cys Leu Ser
305                 310                 315                 320

Asp Ser Ala Ile Phe Val Gln Ser Pro Asn Cys Asn Gln Arg Tyr Gly
                325                 330                 335

Trp His Pro Ala Thr Val Cys Lys Ile Pro Pro Gly Cys Asn Leu Lys
            340                 345                 350

Ile Phe Asn Asn Gln Glu Phe Ala Ala Leu Leu Ala Gln Ser Val Asn
        355                 360                 365

Gln Gly Phe Glu Ala Val Tyr Gln Leu Thr Arg Met Cys Thr Ile Arg
        370                 375                 380

Met Ser Phe Val Lys Gly Trp Gly Ala Glu Tyr Arg Arg Gln Thr Val
385                 390                 395                 400

Thr Ser Thr Pro Cys Trp Ile Glu Leu His Leu Asn Gly Pro Leu Gln
                405                 410                 415

Trp Leu Asp Lys Val Leu Thr Gln Met Gly Ser Pro Ser Ile Arg Cys
            420                 425                 430

Ser Ser Val Ser
        435

<210> SEQ ID NO 7
<211> LENGTH: 2449
<212> TYPE: DNA
<213> ORGANISM: Homo sapiens

<400> SEQUENCE: 7
cccccctcat catcatcatc aatcaatcaa tcaattttac ttacctcctc ctctacctct     60
actcagttca gttactcatc atacaataat aattacaatt actcagattc acactacaat    120
gagtctcaat gagtctcaat gagtctcaat gagtctcaat gagtctcaat gagtcagaaa    180
aaaaaaatga tctactacat aggacataat aaactctcat atctcataac acccatacta    240

-continued

```
cgtgactcac tatagggctc gagcggccgc ctgggcaggt gcttaggacc tgtgtatgac    300
gtttcacctg tgatctgttc tttcggtagc cactgacttt gagttacagg aaggtctccg    360
aagatttgtg tcaaatgacg tcaatggcca gcttgttttc ttttactagt ccagcagtaa    420
agcgattgtt gggctggaaa caaggtgatg aggaggagaa atgggcagaa aaggcagttg    480
atgctttggt gaagaaacta aaaagaaaa agggtgccat ggaggaactg gagaaagcct    540
tgagcagtcc aggacagccg agtaaatgtg tcactattcc cagatcttta gatggacgcc    600
tgcaggtttc tcacagaaaa ggcttacccc atgttatata ttgtcgtgtt tggcgctggc    660
cggatttgca gagtcatcat gagctaaagc cgttggatat ttgtgaattt ccttttggat    720
ctaagcaaaa agaagtttgt atcaacccat accactataa gagagtggag agtccagtct    780
tacctccagt attagtgcct cgtcataatg aattcaatcc acaacacagc cttctggttc    840
agtttaggaa cctgagccac aatgaaccac acatgccaca aaatgccacg tttccacatt    900 cttttccacca gcccaacaac actccttttc ccttatctcc aaacagccct tatcccccctt   960 ctcctgctag cagcacatat cccaactccc cagcaagttc tggaccagga agtccatttc   1020
agctcccagc tgatacgcct cctcctgcct atatgccacc tgatgatcag atgggtcaag   1080
atccttccca gcctatggat acaagcaata atatgattcc tcagattatg cccagtatat   1140
ccagcaggga tgttcagcct gttgcctatg aagagcctaa acattggtgt tcaatagtct   1200
actatgaatt aaacaatcgt gttggagaag ctttttcatgc atcttctact cgtgtgttag   1260
tagatggatt cacagatcct tcaaataaca aaagtagatt ctgcttgggt ttgttgtcaa   1320
atgttaatcg taattcgaca attgaaaaca ctaggcgaca tattggaaaa ggtgttcatc   1380
tgtactatgt tggtggagag gtgtatgcgg aatgcctcag tgacagcagc atatttgtac   1440
agagtaggaa ctgcaacttt catcatggct ttcatcccac cactgtctgt aagattccca   1500
gcagctgcag cctcaaaatt tttaacaatc aggagtttgc tcagcttctg gctcaatctg   1560
tcaaccatgg gtttgaggca gtatatgagc tcaccaaaat gtgtaccatt cggatgagtt   1620
ttgtcaaggt tgggagca gaatatcacc ggcaggatgt aaccagcacc ccatgttgga   1680
ttgagattca tcttcatggg cctcttcagt ggctggataa agtccttact cagatgggct   1740
cccctctgaa ccccatatct tctgtttcat aatgcagaag tattcttttc aattatattg   1800
ttagtggact tgttttaatt ttagagaaac tttgagtaca gatactgtga gcttacattg   1860
aaaacagata ttcagctta ttttttcta cataattgtg accaatacat ttgtattttg   1920
tgatgaatct acatttgttt gtattcatgt tcatgtgatt aactcttaga agtgttgtaa   1980
aagatgcaga gtaagtatta tgccccagtt cagaaatttg gcattgatct taaactggaa   2040
catgctttta ctttattgcc ctaacaattt tttattaaat ttatttgaaa atgcatcaca   2100
tgatgaaaaa ttatagctta taagagggca tatacagtga agagtaagtt ttccctccta   2160
ctctcgatct tccagaagct gtactttac cagtttcttt gtcccaccaa cttaaaaaaa   2220
aaaagtacaa ttcattgttt tgcaaaagtg tatggtaggg gcttaaaaga aactataaag   2280
ttttatttga atgaacacta tgcactgctg taactggtag tgttcagtaa aagcaaaatg   2340
atagttttct agatgacata aaatttacat ttaatacaga taagtgttct tcagtgtaat   2400
gtgacttcat gctatatatc ttttgtaaga catttccttt tttaaaaaa              2449
```

<210> SEQ ID NO 8
<211> LENGTH: 465
<212> TYPE: PRT
<213> ORGANISM: Homo sapiens -continued

<400> SEQUENCE: 8

```
Met Thr Ser Met Ala Ser Leu Phe Ser Phe Thr Ser Pro Ala Val Lys
  1               5                  10                  15

Arg Leu Leu Gly Trp Lys Gln Gly Asp Glu Glu Lys Trp Ala Glu
             20                  25                  30

Lys Ala Val Asp Ala Leu Val Lys Lys Leu Lys Lys Lys Gly Ala
             35                  40                  45

Met Glu Glu Leu Glu Lys Ala Leu Ser Ser Pro Gly Gln Pro Ser Lys
 50                  55                  60

Cys Val Thr Ile Pro Arg Ser Leu Asp Gly Arg Leu Gln Val Ser His
 65                  70                  75                  80

Arg Lys Gly Leu Pro His Val Ile Tyr Cys Arg Val Trp Arg Trp Pro
             85                  90                  95

Asp Leu Gln Ser His His Glu Leu Lys Pro Leu Asp Ile Cys Glu Phe
             100                 105                 110

Pro Phe Gly Ser Lys Gln Lys Glu Val Cys Ile Asn Pro Tyr His Tyr
             115                 120                 125

Lys Arg Val Glu Ser Pro Val Leu Pro Pro Val Leu Val Pro Arg His
 130                 135                 140

Asn Glu Phe Asn Pro Gln His Ser Leu Leu Val Gln Phe Arg Asn Leu
145                 150                 155                 160

Ser His Asn Glu Pro His Met Pro Gln Asn Ala Thr Phe Pro Asp Ser
             165                 170                 175

Phe His Gln Pro Asn Asn Ala Pro Phe Pro Leu Ser Pro Asn Ser Pro
             180                 185                 190

Tyr Pro Pro Ser Pro Ala Ser Ser Thr Tyr Pro Asn Ser Pro Ala Ser
             195                 200                 205

Ser Gly Pro Gly Ser Pro Phe Gln Leu Pro Ala Asp Thr Pro Pro Pro
             210                 215                 220

Ala Tyr Met Pro Pro Asp Asp Gln Met Ala Pro Asp Asn Ser Gln Pro
225                 230                 235                 240

Met Asp Thr Ser Ser Asn Met Ile Pro Gln Thr Met Pro Ser Ile Ser
             245                 250                 255

Ser Arg Asp Val Gln Pro Val Ala Tyr Glu Glu Pro Lys His Trp Cys
             260                 265                 270

Ser Ile Val Tyr Tyr Glu Leu Asn Asn Arg Val Gly Glu Ala Phe His
             275                 280                 285

Ala Ser Ser Thr Ser Val Leu Val Asp Gly Phe Thr Asp Pro Ser Asn
             290                 295                 300

Asn Lys Ser Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
             325                 330                 335

Tyr Tyr Val Gly Gly Glu Val Tyr Ala Glu Cys Leu Ser Asp Ser Ser
             340                 345                 350

Ile Phe Val Gln Ser Arg Asn Cys Asn Phe His His Gly Phe His Pro
             355                 360                 365

Thr Thr Val Cys Lys Ile Pro Ser Ser Cys Ser Leu Lys Ile Phe Asn
             370                 375                 380

Asn Gln Glu Phe Ala Gln Leu Leu Ala Gln Ser Val Asn His Gly Phe
385                 390                 395                 400

Glu Ala Val Tyr Glu Leu Thr Lys Met Cys Thr Ile Arg Met Ser Phe
```

| | 405 | | 410 | | | 415 | | |
|---|---|---|---|---|---|---|---|---|

Val Lys Gly Trp Gly Ala Glu Tyr His Arg Gln Asp Val Thr Ser Thr
              420                  425              430

Pro Cys Trp Ile Glu Ile His Leu His Gly Pro Leu Gln Trp Leu Asp
              435                  440              445

Lys Val Leu Thr Gln Met Gly Ser Pro Leu Asn Pro Ile Ser Ser Val
   450                    455              460

Ser
465

<210> SEQ ID NO 9
<211> LENGTH: 2037
<212> TYPE: DNA
<213> ORGANISM: Homo sapiens

<400> SEQUENCE: 9

| | | | | | |
|---|---|---|---|---|---|
| cccccctcat | catcatcatc | aatcaatcaa | tcaattttac | ttacctcctc | ctctacctct | 60 |
| actcagttca | gttactcatc | atacaataat | aattacaatt | actcagattc | acactacaat | 120 |
| gagtctcaat | gagtctcaat | gagtctcaat | gagtctcaat | gagtctcaat | gagtcagaaa | 180 |
| aaaaaaatga | tctactacat | aggacataat | aaactctcat | atctcataac | acccatacta | 240 |
| cgtgtcactg | catgtgtatt | cgtgagttcg | cggttgaaca | actgttcctt | tactctgctc | 300 |
| cctgtctttg | tgctgactgg | gttactttt | taaacactag | gaatggtaat | ttctactctt | 360 |
| ctggacttca | aactaagaag | ttaaagagac | ttctctgtaa | ataaacaaat | ctcttctgct | 420 |
| gtccttttgc | atttggagac | agctttattt | caccatatcc | aaggagtata | actagtgctg | 480 |
| tcattatgaa | tgtgacaagt | ttattttcct | ttacaagtcc | agctgtgaag | agacttcttg | 540 |
| ggtggaaaca | gggcgatgaa | gaagaaaaat | gggcagagaa | agctgttgat | gctttggtga | 600 |
| aaaaactgaa | gaaaaagaaa | ggtgccatgg | aggaactgga | aaaggccttg | agctgcccag | 660 |
| ggcaaccgag | taactgtgtc | accattcccc | gctctctgga | tggcaggctg | caagtctccc | 720 |
| accggaaggg | actgcctcat | gtcatttact | gccgtgtgtg | gcgctggccc | gatcttcaga | 780 |
| gccaccatga | actaaaacca | ctggaatgct | gtgagtttcc | ttttggttcc | aagcagaagg | 840 |
| aggtctgcat | caatccctac | cactataaga | gagtagaaag | ccctgtactt | cctcctgtgc | 900 |
| tggttccaag | acacagcgaa | tataatcctc | agcacagcct | cttagctcag | ttccgtaact | 960 |
| taggacaaaa | tgagcctcac | atgccactca | acgccacttt | tccagattct | ttccagcaac | 1020 |
| ccaacagcca | cccgtttcct | cactctccca | atagcagtta | cccaaactct | cctgggagca | 1080 |
| gcagcagcac | ctaccctcac | tctcccacca | gctcagaccc | aggaagccct | ttccagatgc | 1140 |
| cagctgatac | gcccccacct | gcttacctgc | ctcctgaaga | ccccatgacc | caggatggct | 1200 |
| ctcagccgat | ggacacaaac | atgatggcgc | ctcccctgcc | ctcagaaatc | aacagaggag | 1260 |
| atgttcaggc | ggttgcttat | gaggaaccaa | aacactggtg | ctctattgtc | tactatgagc | 1320 |
| tcaacaatcg | tgtgggtgaa | gcgttccatg | cctcctccac | aagtgtgttg | gtggatggtt | 1380 |
| tcactgatcc | ttccaacaat | aagaaccgtt | tctgccttgg | gctgctctcc | aatgttaacc | 1440 |
| ggaattccac | tattgaaaac | accaggcgga | atattggaaa | aggagttcat | ctttattatg | 1500 |
| ttggagggga | ggtgtatgcc | gaatgcctta | gtgacagtag | catctttgtg | caaagtcgga | 1560 |
| actgcaacta | ccatcatgga | tttcatccta | ctactgttg | caagatccct | agtgggtgta | 1620 |
| gtctgaaaat | ttttaacaac | caagaatttg | ctcagttatt | ggcacagtct | gtgaaccatg | 1680 |
| gatttgagac | agtctatgag | cttacaaaaa | tgtgtactat | acgtatgagc | tttgtgaagg | 1740 |

-continued

```
gctgggagc agaataccac cgccaggatg ttactagcac cccctgctgg attgagatac   1800
atctgcacgg cccctccag tggctggata agttcttac tcaaatgggt tcacctcata   1860
atcctatttc atctgtatct taaatggccc caggcatctg cctctggaaa actattgagc   1920
cttgcatgta cttgaaggat ggatgagtca gacacgattg agaactgaca aaggagcctt   1980
gataatactt gacctctgtg accaactgtt ggattcagaa atttaaacaa aaaaaaa     2037
```

<210> SEQ ID NO 10
<211> LENGTH: 475
<212> TYPE: PRT
<213> ORGANISM: Homo sapiens

<400> SEQUENCE: 10

```
Val Ala Met Ile Asn Ala Cys Ile Asp Ser Met Asn Val Thr Ser Leu
 1               5                  10                  15

Phe Ser Phe Thr Ser Pro Ala Val Lys Arg Leu Leu Gly Trp Lys Gln
             20                  25                  30

Gly Asp Glu Glu Glu Lys Trp Ala Glu Lys Ala Val Asp Ala Leu Val
         35                  40                  45

Lys Lys Leu Lys Lys Lys Lys Gly Ala Met Glu Glu Leu Glu Lys Ala
     50                  55                  60

Leu Ser Cys Pro Gly Gln Pro Ser Asn Cys Val Thr Ile Pro Arg Ser
 65                  70                  75                  80

Leu Asp Gly Arg Leu Gln Val Ser His Arg Lys Gly Leu Pro His Val
                 85                  90                  95

Ile Tyr Cys Arg Val Trp Arg Trp Pro Asp Leu Gln Ser His His Glu
            100                 105                 110

Leu Lys Pro Leu Glu Cys Cys Glu Phe Pro Phe Gly Ser Lys Gln Lys
        115                 120                 125

Glu Val Cys Ile Asn Pro Tyr His Tyr Lys Arg Val Glu Ser Pro Val
    130                 135                 140

Leu Pro Pro Val Leu Val Pro Arg His Ser Glu Tyr Asn Pro Gln His
145                 150                 155                 160

Ser Leu Leu Ala Gln Phe Arg Asn Leu Gly Gln Asn Glu Pro His Met
                165                 170                 175

Pro Leu Asn Ala Thr Phe Pro Asp Ser Phe Gln Gln Pro Asn Ser His
            180                 185                 190

Pro Phe Pro His Ser Pro Asn Ser Ser Tyr Pro Asn Ser Pro Gly Ser
        195                 200                 205

Ser Ser Ser Thr Tyr Pro His Ser Pro Thr Ser Asp Pro Gly Ser
    210                 215                 220

Pro Phe Gln Met Pro Ala Asp Thr Pro Pro Ala Tyr Leu Pro Pro
225                 230                 235                 240

Glu Asp Pro Met Thr Gln Asp Gly Ser Gln Pro Met Asp Thr Asn Met
                245                 250                 255

Met Ala Pro Pro Leu Pro Ser Glu Ile Asn Arg Gly Asp Val Gln Ala
            260                 265                 270

Val Ala Tyr Glu Glu Pro Lys His Trp Cys Ser Ile Val Tyr Tyr Glu
        275                 280                 285

Leu Asn Asn Arg Val Gly Glu Ala Phe His Ala Ser Ser Thr Ser Val
    290                 295                 300

Leu Val Asp Gly Phe Thr Asp Pro Ser Asn Asn Lys Asn Arg Phe Cys
305                 310                 315                 320
```

-continued

```
Leu Gly Leu Leu Ser Asn Val Asn Arg Asn Ser Thr Ile Glu Asn Thr
            325                 330                 335

Arg Arg His Ile Gly Lys Gly Val His Leu Tyr Tyr Val Gly Gly Glu
            340                 345                 350

Val Tyr Ala Glu Cys Leu Ser Asp Ser Ser Ile Phe Val Gln Ser Arg
            355                 360                 365

Asn Cys Asn Tyr His His Gly Phe His Pro Thr Thr Val Cys Lys Ile
            370                 375                 380

Pro Ser Gly Cys Ser Leu Lys Ile Phe Asn Asn Gln Glu Phe Ala Gln
385                 390                 395                 400

Leu Leu Ala Gln Ser Val Asn His Gly Phe Glu Thr Val Tyr Glu Leu
            405                 410                 415

Thr Lys Met Cys Thr Ile Arg Met Ser Phe Val Lys Gly Trp Gly Ala
            420                 425                 430

Glu Tyr His Arg Gln Asp Val Thr Ser Thr Pro Cys Trp Ile Glu Ile
            435                 440                 445

His Leu His Gly Pro Leu Gln Trp Leu Asp Lys Val Leu Thr Gln Met
            450                 455                 460

Gly Ser Pro His Asn Pro Ile Ser Ser Val Ser
465                 470                 475

<210> SEQ ID NO 11
<211> LENGTH: 456
<212> TYPE: PRT
<213> ORGANISM: Drosophila melanogaster

<400> SEQUENCE: 11

Met Asp Thr Asp Val Glu Ser Asn Thr Ser Ser Ala Met Ser Thr
  1               5                  10                  15

Leu Gly Ser Leu Phe Ser Phe Thr Ser Pro Ala Val Lys Lys Leu Leu
             20                  25                  30

Gly Trp Lys Gln Gly Asp Glu Glu Lys Trp Ala Glu Lys Ala Val
             35                  40                  45

Asp Ser Leu Val Lys Lys Leu Lys Arg Lys Gly Ala Ile Glu Glu
 50                  55                  60

Leu Glu Arg Ala Leu Ser Cys Pro Gly Gln Pro Ser Lys Cys Val Thr
 65                  70                  75                  80

Ile Pro Arg Ser Leu Asp Gly Arg Leu Gln Val Ser His Arg Lys Gly
             85                  90                  95

Leu Pro His Val Ile Tyr Cys Arg Val Trp Arg Trp Pro Asp Leu Gln
            100                 105                 110

Ser His His Glu Leu Lys Pro Leu Glu Leu Cys Gln Tyr Pro Phe Ser
            115                 120                 125

Ala Lys Gln Lys Glu Val Cys Ile Asn Pro Tyr His Tyr Lys Arg Val
130                 135                 140

Glu Ser Pro Val Leu Pro Pro Val Leu Val Pro Arg His Ser Glu Phe
145                 150                 155                 160

Ala Pro Gly His Ser Met Leu Gln Phe Asn His Val Ala Glu Pro Ser
            165                 170                 175

Met Pro His Asn Val Ser Tyr Ser Asn Ser Gly Phe Asn Ser His Ser
            180                 185                 190

Leu Ser Thr Ser Asn Thr Ser Val Gly Ser Pro Ser Ser Val Asn Ser
            195                 200                 205

Asn Pro Asn Ser Pro Tyr Asp Ser Leu Ala Gly Thr Pro Pro Pro Ala
210                 215                 220
```

Tyr Ser Pro Ser Glu Asp Gly Asn Ser Asn Pro Asn Asp Gly Gly
225                 230                 235                 240

Gln Leu Leu Asp Ala Gln Met Gly Asp Val Ala Gln Val Ser Tyr Ser
            245                 250                 255

Glu Pro Ala Phe Trp Ala Ser Ile Ala Tyr Tyr Glu Leu Asn Cys Arg
            260                 265                 270

Val Gly Glu Val Phe His Cys Asn Asn Asn Ser Val Leu Val Asp Gly
        275                 280                 285

Phe Thr Asn Pro Ser Asn Asn Ser Asp Arg Cys Cys Leu Gly Gln Leu
    290                 295                 300

Ser Asn Val Asn Arg Asn Ser Thr Ile Glu Asn Thr Arg Arg His Ile
305                 310                 315                 320

Gly Lys Gly Val His Leu Tyr Tyr Val Thr Gly Glu Val Tyr Ala Glu
                325                 330                 335

Cys Leu Ser Asp Ser Ala Ile Phe Val Gln Ser Arg Asn Cys Asn Tyr
            340                 345                 350

His His Gly Phe His Pro Ser Thr Val Cys Lys Ile Pro Pro Gly Cys
                355                 360                 365

Ser Leu Lys Ile Phe Asn Asn Gln Glu Phe Ala Gln Leu Leu Ser Gln
    370                 375                 380

Ser Val Asn Asn Gly Phe Glu Ala Val Tyr Glu Leu Thr Lys Met Cys
385                 390                 395                 400

Thr Ile Arg Met Ser Phe Val Lys Gly Trp Gly Ala Glu Tyr His Arg
                405                 410                 415

Gln Asp Val Thr Ser Thr Pro Cys Trp Ile Glu Ile His Leu His Gly
            420                 425                 430

Pro Leu Gln Trp Leu Asp Lys Val Leu Thr Gln Met Gly Ser Pro His
        435                 440                 445

Asn Ala Ile Ser Ser Val Ser Pro
        450                 455

<210> SEQ ID NO 12
<211> LENGTH: 54
<212> TYPE: PRT
<213> ORGANISM: C. elegans

<400> SEQUENCE: 12

Arg Asp Phe Cys Thr Ile Ala Ile Ser Phe Val Lys Ala Trp Gly Asp
1               5                   10                  15

Asx Tyr Arg Lys Thr Ile Lys Glu Thr Pro Cys Trp Ile Glu Val Thr
            20                  25                  30

Leu His Arg Pro Leu Gln Ile Leu Asp Gln Leu Leu Lys Asn Ser Ser
        35                  40                  45

Gln Phe Gly Ser Ser Pro
    50

<210> SEQ ID NO 13
<211> LENGTH: 61
<212> TYPE: PRT
<213> ORGANISM: C. elegans

<400> SEQUENCE: 13

Ser Lys His Cys Phe Ile Arg Ile Ser Phe Val Lys Gly Trp Gly Glu
1               5                   10                  15

Asp Tyr Pro Arg Gln Asp Val Thr Ser Thr Pro Cys Trp Leu Glu Leu
            20                  25                  30

Arg Leu Asn Val Pro Leu Ala Tyr Ile Asp Gln Lys Met Lys Gln Thr
            35                  40                  45

Pro Arg Thr Asn Leu Met Glu Pro Asn Ser Met Thr Pro
     50                  55                  60

<210> SEQ ID NO 14
<211> LENGTH: 59
<212> TYPE: PRT
<213> ORGANISM: C. elegans

<400> SEQUENCE: 14

Gln Lys Met Thr Phe Ile Arg Met Ser Phe Val Lys Gly Trp Gly Ala
 1               5                  10                  15

Glu Tyr Arg Gln Asp Val Thr Ser Thr Pro Cys Trp Ile Glu Ile His
            20                  25                  30

Leu His Ala Pro Leu Ala Trp Leu Asp Arg Val Leu Ser Thr Met Gly
            35                  40                  45

Pro Thr Pro Arg Pro Ile Ser Ser Ile Ser Pro
     50                  55

<210> SEQ ID NO 15
<211> LENGTH: 58
<212> TYPE: PRT
<213> ORGANISM: Homo sapiens

<400> SEQUENCE: 15

Arg Arg Leu Cys Ile Leu Arg Met Ser Phe Val Lys Gly Trp Gly Pro
 1               5                  10                  15

Asp Tyr Pro Arg Gln Ser Ile Lys Glu Thr Pro Cys Trp Ile Glu Ile
            20                  25                  30

His Leu His Arg Ala Leu Gln Leu Leu Asp Glu Val Leu His Thr Met
            35                  40                  45

Pro Ile Ala Asp Pro Gln Pro Leu Asp Pro
     50                  55

<210> SEQ ID NO 16
<211> LENGTH: 19
<212> TYPE: DNA
<213> ORGANISM: Homo sapiens

<400> SEQUENCE: 16
gtccatcttg ccattcacg                                              19

<210> SEQ ID NO 17
<211> LENGTH: 20
<212> TYPE: DNA
<213> ORGANISM: Homo sapiens

<400> SEQUENCE: 17
tggtgatggc tttctcaagc                                             20

<210> SEQ ID NO 18
<211> LENGTH: 21
<212> TYPE: DNA
<213> ORGANISM: Homo sapiens

<400> SEQUENCE: 18
tggacaaaac aagaaagacg c                                           21

<210> SEQ ID NO 19

-continued

<210> SEQ ID NO 19
<211> LENGTH: 21
<212> TYPE: DNA
<213> ORGANISM: Homo sapiens

<400> SEQUENCE: 19
caaaaaccat acaccaaacc c                                          21

<210> SEQ ID NO 20
<211> LENGTH: 19
<212> TYPE: DNA
<213> ORGANISM: Homo sapiens

<400> SEQUENCE: 20
tgggctcccc aagcatccg                                             19

<210> SEQ ID NO 21
<211> LENGTH: 21
<212> TYPE: DNA
<213> ORGANISM: Homo sapiens

<400> SEQUENCE: 21
ttccttgaca acaatgggtt g                                          21

<210> SEQ ID NO 22
<211> LENGTH: 22
<212> TYPE: DNA
<213> ORGANISM: Homo sapiens

<400> SEQUENCE: 22
taaacattgg tgttcaatag tc                                         22

<210> SEQ ID NO 23
<211> LENGTH: 22
<212> TYPE: DNA
<213> ORGANISM: Homo sapiens

<400> SEQUENCE: 23
tgttttcaat tgtcgaatta cg                                         22

<210> SEQ ID NO 24
<211> LENGTH: 21
<212> TYPE: DNA
<213> ORGANISM: Homo sapiens

<400> SEQUENCE: 24
tcaatcgtgt ctgactcatc c                                          21

<210> SEQ ID NO 25
<211> LENGTH: 18
<212> TYPE: DNA
<213> ORGANISM: Homo sapiens

<400> SEQUENCE: 25
gagcagaata ccaccgcc                                              18

<210> SEQ ID NO 26
<211> LENGTH: 58
<212> TYPE: DNA
<213> ORGANISM: Homo sapiens

<400> SEQUENCE: 26
ggatcctaat acgactcact atagggagac caccatgggt aagaacatgt cgtccatc  58

-continued

```
<210> SEQ ID NO 27
<211> LENGTH: 20
<212> TYPE: DNA
<213> ORGANISM: Homo sapiens

<400> SEQUENCE: 27
tttccatggg acttgattgg                                              20

<210> SEQ ID NO 28
<211> LENGTH: 35
<212> TYPE: DNA
<213> ORGANISM: Homo sapiens

<400> SEQUENCE: 28
accaccatgg caccatatcc aaggagtata actag                             35

<210> SEQ ID NO 29
<211> LENGTH: 34
<212> TYPE: DNA
<213> ORGANISM: Homo sapiens

<400> SEQUENCE: 29 tttttttatat gaatccaaca gttggtcaca gagg                             34

<210> SEQ ID NO 30
<211> LENGTH: 30
<212> TYPE: DNA
<213> ORGANISM: Homo sapiens

<400> SEQUENCE: 30
accaccatgg gtaagaacat gtcgtccatc                                   30

<210> SEQ ID NO 31
<211> LENGTH: 20
<212> TYPE: DNA
<213> ORGANISM: Homo sapiens

<400> SEQUENCE: 31
tttccatggg acttgattgg                                              20

<210> SEQ ID NO 32
<211> LENGTH: 22
<212> TYPE: DNA
<213> ORGANISM: Homo sapiens

<400> SEQUENCE: 32
gagccagcca tgtcgtccat cc                                           22

<210> SEQ ID NO 33
<211> LENGTH: 20
<212> TYPE: DNA
<213> ORGANISM: Homo sapiens

<400> SEQUENCE: 33
ttttccccaa gcctgccctc                                              20

<210> SEQ ID NO 34
<211> LENGTH: 30
<212> TYPE: DNA
<213> ORGANISM: Homo sapiens

<400> SEQUENCE: 34
accaccatgg tctccgaaga tttgtgtcaa                                   30
```

<210> SEQ ID NO 35
<211> LENGTH: 33
<212> TYPE: DNA
<213> ORGANISM: Homo sapiens

<400> SEQUENCE: 35 tttttatat ctgttttcaa tgtaagctca cag                               33

<210> SEQ ID NO 36
<211> LENGTH: 30
<212> TYPE: DNA
<213> ORGANISM: Homo sapiens

<400> SEQUENCE: 36
accaccatgg aatctccgcc acctccctac                                  30

<210> SEQ ID NO 37
<211> LENGTH: 19
<212> TYPE: DNA
<213> ORGANISM: Homo sapiens

<400> SEQUENCE: 37
ccgccactat ctggggttg                                              19

<210> SEQ ID NO 38
<211> LENGTH: 59
<212> TYPE: PRT
<213> ORGANISM: Homo sapiens

<400> SEQUENCE: 38

Thr Arg Met Cys Thr Ile Arg Met Ser Phe Val Lys Gly Trp Gly Ala
 1               5                  10                  15

Glu Tyr Arg Arg Gln Thr Val Thr Ser Thr Pro Cys Trp Ile Glu Leu
            20                  25                  30

His Leu Asn Gly Pro Leu Gln Trp Leu Asp Lys Val Leu Thr Gln Met
        35                  40                  45

Gly Ser Pro Ser Val Arg Cys Ser Ser Met Ser
    50                  55

<210> SEQ ID NO 39
<211> LENGTH: 59
<212> TYPE: PRT
<213> ORGANISM: Homo sapiens

<400> SEQUENCE: 39

Thr Lys Met Cys Thr Ile Arg Met Ser Phe Val Lys Gly Trp Gly Ala
 1               5                  10                  15

Glu Tyr His Arg Gln Asp Val Thr Ser Thr Pro Cys Trp Ile Glu Ile
            20                  25                  30

His Leu His Gly Pro Leu Gln Trp Leu Asp Lys Val Leu Thr Gln Met
        35                  40                  45

Gly Ser Pro His Asn Pro Ile Ser Ser Val Ser
    50                  55

<210> SEQ ID NO 40
<211> LENGTH: 38
<212> TYPE: PRT
<213> ORGANISM: Homo sapiens

<400> SEQUENCE: 40

Tyr Asp Pro Asn Ser Val Arg Ile Ser Phe Ala Lys Gly Trp Gly Pro

-continued

```
                1               5                   10                  15
Cys Tyr Ser Arg Gln Phe Ile Thr Ser Cys Pro Cys Trp Leu Glu Ile
                    20                  25                  30

Leu Leu Asn Asn Pro Arg
            35
```

<210> SEQ ID NO 41
<211> LENGTH: 59
<212> TYPE: PRT
<213> ORGANISM: Homo sapiens

<400> SEQUENCE: 41

```
Thr Arg Met Cys Thr Ile Arg Met Ser Phe Val Lys Gly Trp Gly Ala
1               5                   10                  15

Glu Tyr Arg Arg Gln Thr Val Thr Ser Thr Pro Cys Trp Ile Glu Leu
                20                  25                  30

His Leu Asn Gly Pro Leu Gln Trp Leu Asp Lys Val Leu Thr Gln Met
            35                  40                  45

Gly Ser Pro Ser Ile Arg Cys Ser Ser Val Ser
        50                  55
```

<210> SEQ ID NO 42
<211> LENGTH: 467
<212> TYPE: PRT
<213> ORGANISM: Homo sapiens

<400> SEQUENCE: 42

```
Met Ser Ser Ile Leu Pro Phe Thr Pro Pro Val Val Lys Arg Leu Leu
1               5                   10                  15

Gly Trp Lys Lys Ser Ala Gly Gly Ser Gly Gly Ala Gly Gly Gly Glu
                20                  25                  30

Gln Asn Gly Gln Glu Glu Lys Trp Cys Glu Lys Ala Val Lys Ser Leu
            35                  40                  45

Val Lys Lys Leu Lys Lys Thr Gly Arg Leu Asp Glu Leu Glu Lys Ala
        50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Pro Asn Thr Ile Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
        130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
        195                 200                 205

Gly Ile Glu Pro Gln Ser Asn Tyr Ile Pro Glu Thr Pro Pro Pro Gly
        210                 215                 220

Tyr Ile Ser Glu Asp Gly Glu Thr Ser Asp Gln Gln Leu Asn Gln Ser
```

```
                 225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
                260                 265                 270

Phe Trp Cys Ser Ile Ala Tyr Tyr Glu Leu Asn Gln Arg Val Gly Glu
                275                 280                 285

Thr Phe His Ala Ser Gln Pro Ser Leu Thr Val Asp Gly Phe Thr Asp
                290                 295                 300

Pro Ser Asn Ser Glu Arg Phe Cys Leu Gly Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
                340                 345                 350

Ser Ala Ile Phe Val Gln Ser Pro Asn Cys Asn Gln Arg Tyr Gly Trp
                355                 360                 365

His Pro Ala Thr Val Cys Lys Ile Pro Pro Gly Cys Asn Leu Lys Ile
                370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415

Ser Phe Val Lys Gly Trp Gly Ala Glu Tyr Arg Arg Gln Thr Val Thr
                420                 425                 430

Ser Thr Pro Cys Trp Ile Glu Leu His Leu Asn Gly Pro Leu Gln Trp
                435                 440                 445

Leu Asp Lys Val Leu Thr Gln Met Gly Ser Pro Ser Val Arg Cys Ser
        450                 455                 460

Ser Met Ser
465

<210> SEQ ID NO 43
<211> LENGTH: 455
<212> TYPE: PRT
<213> ORGANISM: D. melanogaster

<400> SEQUENCE: 43

Met Asp Thr Asp Val Glu Ser Asn Thr Ser Ser Ala Met Ser Thr
1               5                   10                  15

Leu Gly Ser Leu Phe Ser Phe Thr Ser Pro Ala Val Lys Lys Leu Leu
                20                  25                  30

Gly Trp Lys Gln Gly Asp Glu Glu Lys Trp Ala Glu Lys Ala Val
                35                  40                  45

Asp Ser Leu Val Lys Lys Leu Lys Arg Lys Gly Ala Ile Glu Glu
        50                  55                  60

Leu Glu Arg Ala Leu Ser Cys Pro Gly Gln Pro Ser Lys Cys Val Thr
65                  70                  75                  80

Ile Pro Arg Ser Leu Asp Gly Arg Leu Gln Val Ser His Arg Lys Gly
                85                  90                  95

Leu Pro His Val Ile Tyr Cys Arg Val Trp Arg Trp Pro Asp Leu Gln
                100                 105                 110

Ser His His Glu Leu Lys Pro Leu Glu Leu Cys Gln Tyr Pro Phe Ser
                115                 120                 125
```

```
Ala Lys Gln Lys Glu Val Cys Ile Asn Pro Tyr His Tyr Lys Arg Val
    130                 135                 140

Glu Ser Pro Val Leu Pro Val Leu Val Pro Arg His Ser Glu Phe
145                 150                 155                 160

Ala Pro Gly His Ser Met Leu Gln Phe Asn His Val Ala Glu Pro Ser
                165                 170                 175

Met Pro His Asn Val Ser Tyr Ser Asn Ser Gly Phe Asn Ser His Ser
            180                 185                 190

Leu Ser Thr Ser Asn Thr Ser Val Gly Ser Pro Ser Ser Val Asn Ser
        195                 200                 205

Asn Pro Asn Ser Pro Tyr Asp Ser Leu Ala Gly Thr Pro Pro Ala
    210                 215                 220

Tyr Ser Pro Ser Glu Asp Gly Asn Ser Asn Pro Asn Asp Gly Gly
225                 230                 235                 240

Gln Leu Leu Asp Ala Gln Met Gly Asp Val Ala Gln Val Ser Tyr Ser
                245                 250                 255

Glu Pro Ala Phe Trp Ala Ser Ile Ala Tyr Tyr Glu Leu Asn Cys Arg
            260                 265                 270

Val Gly Glu Val Phe His Cys Asn Asn Asn Ser Val Ile Val Asp Gly
        275                 280                 285

Phe Thr Asn Pro Ser Asn Asn Ser Asp Arg Cys Cys Leu Gly Gln Leu
    290                 295                 300

Ser Asn Val Asn Arg Asn Ser Thr Ile Glu Asn Thr Arg Arg His Ile
305                 310                 315                 320

Gly Lys Gly Val His Leu Tyr Tyr Val Thr Gly Glu Val Tyr Ala Glu
                325                 330                 335

Cys Leu Ser Asp Ser Ala Ile Phe Val Gln Ser Arg Asn Cys Asn Tyr
            340                 345                 350

His His Gly Phe His Pro Ser Thr Val Cys Lys Ile Pro Pro Gly Cys
        355                 360                 365

Ser Leu Lys Ile Phe Asn Asn Gln Glu Phe Ala Gln Leu Leu Ser Gln
    370                 375                 380

Ser Val Asn Asn Gly Phe Glu Ala Val Tyr Glu Leu Thr Lys Met Cys
385                 390                 395                 400

Thr Ile Arg Met Ser Phe Val Lys Gly Trp Gly Ala Glu Tyr His Arg
                405                 410                 415

Gln Asp Val Thr Ser Thr Pro Cys Trp Ile Glu Ile His Leu His Gly
            420                 425                 430

Pro Leu Gln Trp Leu Asp Lys Val Leu Thr Gln Met Gly Ser Pro His
        435                 440                 445

Asn Ala Ile Ser Ser Val Ser
    450                 455

<210> SEQ ID NO 44
<211> LENGTH: 71
<212> TYPE: PRT
<213> ORGANISM: Homo sapiens

<400> SEQUENCE: 44

Thr Tyr Arg Thr Tyr Arg Ile Leu Glu Gly Leu Tyr Gly Leu Tyr Gly
1                   5                   10                  15

Leu Val Ala Leu Pro His Glu Ala Leu Ala Gly Leu Cys Tyr Ser Leu
                20                  25                  30

Glu Ser Glu Arg Ala Ser Pro Ser Glu Arg Ala Leu Ala Ile Leu Glu
            35                  40                  45
```

-continued

Pro His Glu Val Ala Leu Gly Leu Asn Ser Glu Arg Pro Arg Ala Ser
    50                  55                  60

Asn Cys Tyr Ser Ala Ser Asn
65                  70

<210> SEQ ID NO 45
<211> LENGTH: 75
<212> TYPE: DNA
<213> ORGANISM: Homo sapiens

<400> SEQUENCE: 45
tactacatag gtgggaagt ttttgctgag tgcctaagtg atagtgcaat ctttgtgcag      60
agccccaatt gtaat                                                     75

<210> SEQ ID NO 46
<211> LENGTH: 31
<212> TYPE: PRT
<213> ORGANISM: Homo sapiens

<400> SEQUENCE: 46

Thr Tyr Arg Thr Tyr Arg Ile Leu Glu Gly Leu Tyr Gly Leu Tyr Gly
 1               5                  10                  15

Leu Ser Glu Arg Pro Arg Ala Ser Asn Cys Tyr Ser Ala Ser Asn
            20                  25                  30

<210> SEQ ID NO 47
<211> LENGTH: 33
<212> TYPE: DNA
<213> ORGANISM: Homo sapiens

<400> SEQUENCE: 47
tactacatag gtgggagag ccccaattgt aat                                  33

<210> SEQ ID NO 48
<211> LENGTH: 465
<212> TYPE: PRT
<213> ORGANISM: Homo sapiens

<400> SEQUENCE: 48

Met Thr Ser Met Ala Ser Leu Phe Ser Phe Thr Ser Pro Ala Val Lys
 1               5                  10                  15

Arg Leu Leu Gly Trp Lys Gln Gly Asp Glu Glu Glu Lys Trp Ala Glu
            20                  25                  30

Lys Ala Val Asp Ala Leu Val Lys Lys Leu Lys Lys Lys Lys Gly Ala
            35                  40                  45

Met Glu Glu Leu Glu Lys Ala Leu Ser Ser Pro Gly Gln Pro Ser Lys
    50                  55                  60

Cys Val Thr Ile Pro Arg Ser Leu Asp Gly Arg Leu Gln Val Ser His
65                  70                  75                  80

Arg Lys Gly Leu Pro His Val Ile Tyr Cys Arg Val Trp Arg Trp Pro
                85                  90                  95

Asp Leu Gln Ser His His Glu Leu Lys Pro Leu Asp Ile Cys Glu Phe
            100                 105                 110

Pro Phe Gly Ser Lys Gln Lys Glu Val Cys Ile Asn Pro Tyr His Tyr
            115                 120                 125

Lys Arg Val Glu Ser Pro Val Leu Pro Pro Val Leu Val Pro Arg His
        130                 135                 140

Asn Glu Phe Asn Pro Gln His Ser Leu Leu Val Gln Phe Arg Asn Leu

```
                145                 150                 155                 160
        Ser His Asn Glu Pro His Met Pro Gln Asn Ala Thr Phe Pro Asp Ser
                        165                 170                 175

Phe His Gln Pro Asn Asn Ala Pro Phe Pro Leu Ser Pro Asn Ser Pro
                        180                 185                 190

Tyr Pro Pro Ser Pro Ala Ser Ser Thr Tyr Pro Asn Ser Pro Ala Ser
                        195                 200                 205

Ser Gly Pro Gly Ser Pro Phe Gln Leu Pro Ala Asp Thr Pro Pro Pro
                        210                 215                 220

Ala Tyr Met Pro Pro Asp Asp Gln Met Ala Pro Asp Asn Ser Gln Pro
        225                 230                 235                 240

Met Asp Thr Ser Ser Asn Met Ile Pro Gln Thr Met Pro Ser Ile Ser
                        245                 250                 255

Ser Arg Asp Val Gln Pro Val Ala Tyr Glu Glu Pro Lys His Trp Cys
                        260                 265                 270

Ser Ile Val Tyr Tyr Glu Leu Asn Asn Arg Val Gly Glu Ala Phe His
                        275                 280                 285

Ala Ser Ser Thr Ser Val Leu Val Asp Gly Phe Thr Asp Pro Ser Asn
        290                 295                 300

Asn Lys Ser Arg Phe Cys Leu Gly Leu Leu Ser Asn Val Asn Arg Asn
        305                 310                 315                 320

Ser Thr Ile Glu Asn Thr Arg Arg His Ile Gly Lys Gly Val His Leu
                        325                 330                 335

Tyr Tyr Val Gly Gly Glu Val Tyr Ala Glu Cys Leu Ser Asp Ser Ser
                        340                 345                 350

Ile Phe Val Gln Ser Arg Asn Cys Asn Phe His His Gly Phe His Pro
                        355                 360                 365

Thr Thr Val Cys Lys Ile Pro Ser Ser Cys Ser Leu Lys Ile Phe Asn
                        370                 375                 380

Asn Gln Glu Phe Ala Gln Leu Leu Ala Gln Ser Val Asn His Gly Phe
        385                 390                 395                 400

Glu Ala Val Tyr Glu Leu Thr Lys Met Cys Thr Ile Arg Met Ser Phe
                        405                 410                 415

Val Lys Gly Trp Gly Ala Glu Tyr His Arg Gln Asp Val Thr Ser Thr
                        420                 425                 430

Pro Cys Trp Ile Glu Ile His Leu His Gly Pro Leu Gln Trp Leu Asp
                        435                 440                 445

Lys Val Leu Thr Gln Met Gly Ser Pro Leu Asn Pro Ile Ser Ser Val
                        450                 455                 460

Ser
        465

<210> SEQ ID NO 49
<211> LENGTH: 235
<212> TYPE: PRT
<213> ORGANISM: Homo sapiens

<400> SEQUENCE: 49

Met Ser Arg Met Gly Lys Pro Ile Glu Thr Gln Lys Ser Pro Pro Pro
        1               5                   10                  15

Pro Tyr Ser Arg Leu Ser Pro Arg Asp Glu Tyr Lys Pro Leu Asp Leu
                        20                  25                  30

Ser Asp Ser Thr Leu Ser Tyr Thr Glu Thr Glu Ala Thr Asn Ser Leu
                        35                  40                  45
```

-continued

```
Ile Thr Ala Pro Gly Glu Phe Ser Asp Ala Ser Met Ser Pro Asp Ala
 50                  55                  60

Thr Lys Pro Ser His Trp Cys Ser Val Ala Tyr Trp Glu His Arg Thr
 65                  70                  75                  80

Arg Val Gly Arg Leu Tyr Ala Val Tyr Asp Gln Ala Val Ser Ile Phe
                 85                  90                  95

Tyr Asp Leu Pro Gln Gly Ser Gly Phe Cys Leu Gly Gln Leu Asn Leu
                100                 105                 110

Glu Gln Arg Ser Glu Ser Val Arg Arg Thr Arg Ser Lys Ile Gly Phe
            115                 120                 125

Gly Ile Leu Leu Ser Lys Glu Pro Asp Gly Val Trp Ala Tyr Asn Arg
130                 135                 140

Gly Glu His Pro Ile Phe Val Asn Ser Pro Thr Leu Asp Ala Pro Gly
145                 150                 155                 160

Gly Arg Ala Leu Val Val Arg Lys Val Pro Pro Gly Tyr Ser Ile Lys
                165                 170                 175

Val Phe Asp Phe Glu Arg Ser Gly Leu Gln His Ala Pro Glu Pro Asp
                180                 185                 190

Ala Ala Asp Gly Pro Tyr Asp Pro Asn Ser Val Arg Ile Ser Phe Ala
            195                 200                 205

Lys Gly Trp Gly Pro Cys Tyr Ser Arg Gln Phe Ile Thr Ser Cys Pro
210                 215                 220

Cys Trp Leu Glu Ile Leu Leu Asn Asn Pro Arg
225                 230                 235

<210> SEQ ID NO 50
<211> LENGTH: 467
<212> TYPE: PRT
<213> ORGANISM: Homo sapiens

<400> SEQUENCE: 50

Met Ser Ser Ile Leu Pro Phe Thr Pro Pro Val Val Lys Arg Leu Leu
 1               5                  10                  15

Gly Trp Lys Lys Ser Ala Gly Gly Ser Gly Gly Ala Gly Gly Gly Glu
                20                  25                  30

Gln Asn Gly Gln Glu Glu Lys Trp Cys Glu Lys Ala Val Lys Ser Leu
            35                  40                  45

Val Lys Lys Leu Lys Lys Thr Gly Arg Leu Asp Glu Leu Glu Lys Ala
 50                  55                  60

Ile Thr Thr Gln Asn Cys Asn Thr Lys Cys Val Thr Ile Pro Ser Thr
 65                  70                  75                  80

Cys Ser Glu Ile Trp Gly Leu Ser Thr Pro Asn Thr Ile Asp Gln Trp
                 85                  90                  95

Asp Thr Thr Gly Leu Tyr Ser Phe Ser Glu Gln Thr Arg Ser Leu Asp
                100                 105                 110

Gly Arg Leu Gln Val Ser His Arg Lys Gly Leu Pro His Val Ile Tyr
            115                 120                 125

Cys Arg Leu Trp Arg Trp Pro Asp Leu His Ser His His Glu Leu Lys
130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
                180                 185                 190
```

-continued

```
Leu Asp Asp Tyr Thr His Ser Ile Pro Glu Asn Thr Asn Phe Pro Ala
        195                 200                 205
Gly Ile Glu Pro Gln Ser Asn Tyr Ile Pro Glu Thr Pro Pro Gly
    210                 215                 220
Tyr Ile Ser Glu Asp Gly Glu Thr Ser Asp Gln Gln Leu Asn Gln Ser
225                 230                 235                 240
Met Asp Thr Gly Ser Pro Ala Glu Leu Ser Pro Thr Thr Leu Ser Pro
                245                 250                 255
Val Asn His Ser Leu Asp Leu Gln Pro Val Thr Tyr Ser Glu Pro Ala
            260                 265                 270
Phe Trp Cys Ser Ile Ala Tyr Tyr Glu Leu Asn Gln Arg Val Gly Glu
        275                 280                 285
Thr Phe His Ala Ser Gln Pro Ser Leu Thr Val Asp Gly Phe Thr Asp
    290                 295                 300
Pro Ser Asn Ser Glu Arg Phe Cys Leu Gly Leu Leu Ser Asn Val Asn
305                 310                 315                 320
Arg Asn Ala Thr Val Glu Met Thr Arg Arg His Ile Gly Arg Gly Val
                325                 330                 335
Arg Leu Tyr Tyr Ile Gly Gly Glu Val Phe Ala Glu Cys Leu Ser Asp
            340                 345                 350
Ser Ala Ile Phe Val Gln Ser Pro Asn Cys Asn Gln Arg Tyr Gly Trp
        355                 360                 365
His Pro Ala Thr Val Cys Lys Ile Pro Pro Gly Cys Asn Leu Lys Ile
    370                 375                 380
Phe Asn Asn Gln Glu Phe Ala Ala Leu Leu Ala Gln Ser Val Asn Gln
385                 390                 395                 400
Gly Phe Glu Ala Val Tyr Gln Leu Thr Arg Met Cys Thr Ile Arg Met
                405                 410                 415
Ser Phe Val Lys Gly Trp Gly Ala Glu Tyr Arg Arg Gln Thr Val Thr
            420                 425                 430
Ser Thr Pro Cys Trp Ile Glu Leu His Leu Asn Gly Pro Leu Gln Trp
        435                 440                 445
Leu Asp Lys Val Leu Thr Gln Met Gly Ser Pro Ser Val Arg Cys Ser
    450                 455                 460
Ser Met Ser
465
```

<210> SEQ ID NO 51
<211> LENGTH: 1921
<212> TYPE: DNA
<213> ORGANISM: Homo sapiens

<400> SEQUENCE: 51

| | | |
|---|---|---|
| ggcggagaag cagctcgcca gccagcagcc cgccagccgc cgggaggttc gatacaagag | 60 |
| gctgttttcc tagcgtggct tgctgccttt ggtaagaaca tgtcgtccat cttgccattc | 120 |
| acgccgccag ttgtgaagag actgctggga tggaagaagt cagctggtgg gtctggagga | 180 |
| gcaggcggag gagagcagaa tgggcaggaa gaaaagtggt gtgagaaagc agtgaaaagt | 240 |
| ctggtgaaga agctaaagaa aacaggacga ttagatgagc ttgagaaagc catcaccact | 300 |
| caaaactgta atactaaatg tgttaccata ccaagcactt gctctgaaat tggggactg | 360 |
| agtacaccaa atacgataga tcagtgggat acaacaggcc tttacagctt ctctgaacaa | 420 |
| accaggtctc ttgatggtcg tctccaggta tcccatcgaa aaggattgcc acatgttata | 480 |

-continued

```
tattgccgat tatggcgctg gcctgatctt cacagtcatc atgaactcaa ggcaattgaa      540
aactgcgaat atgcttttaa tcttaaaaag gatgaagtat gtgtaaaccc ttaccactat      600
acagaacttc cgcctctgga tgactatact cactccattc cagaaaacac taacttccca      660
gcaggaattg agccacagag taattatatt ccagaaacgc cacctcctgg atatatcagt      720
gaagatggag aaacaagtga ccaacagttg aatcaaagta tggacacagg ctctccagca      780
gaactatctc ctactactct ttcccctgtt aatcatagct tggatttaca gccagttact      840
tactcagaac ctgcattttg tgttcgata gcatattatg aattaaatca gagggttgga       900
gaaaccttcc atgcatcaca gccctcactc actgtagatg ctttacaga cccatcaaat       960 tcagagaggt tctgcttagg tttactctcc aatgttaacc gaaatgccac ggtagaaatg     1020
acaagaaggc atataggaag aggagtgcgc ttatactaca taggtgggga agttttttgct    1080 gagtgcctaa gtgatagtgc aatctttgtg cagagcccca attgtaatca gagatatggc     1140
tggcaccctg caacagtgtg taaaattcca ccaggctgta atctgaagat cttcaacaac     1200
caggaatttg ctgctcttct ggctcagtct gttaatcagg gttttgaagc cgtctatcag     1260
ctaactagaa tgtgcaccat aagaatgagt tttgtgaaag ggtggggagc agaataccga     1320
aggcagacgg taacaagtac tccttgctgg attgaacttc atctgaatgg acctctacag     1380
tggttggaca agtattaac tcagatggga tccccttcag tgcgttgctc aagcatgtca      1440
taaagcttca ccaatcaagt cccatggaaa agacttaatg taaacaactc tctctcggtc     1500
aatagcattg gtgttgtggt cccctatgg gactgtttac ctattccaaa aggtttcaag      1560
gagagaaaac cagcacttga ggtcctcatc caattaaagc accttgtgg aatcctgttt       1620 ccctatattt gaatattagg atgggaaaat tagtgtctag aaatactctc cccattaaag     1680
aggaagagaa gattttaaag acttaatgat gtcttattgg gcataaactg agtgtcccaa     1740
aggtttatta ataacagtag tagttatgtg tacaggtaat gtatcatgat ccagtatcac     1800
agtattgtgc tgtttatata catttttagt ttgcatagat gaggtgtgtg tgtgcgctgc     1860
ttcttgatct aggcaaacct ttataaagtt gcagtaccta aaaaaaaaaa aaaaaaaaa      1920 a                                                                    1921
```

<210> SEQ ID NO 52
<211> LENGTH: 465
<212> TYPE: PRT
<213> ORGANISM: Homo sapiens

<400> SEQUENCE: 52

```
Met Thr Ser Met Ala Ser Leu Phe Ser Phe Thr Ser Pro Ala Val Lys
 1               5                  10                  15

Arg Leu Leu Gly Trp Lys Gln Gly Asp Glu Glu Lys Trp Ala Glu
            20                  25                  30

Lys Ala Val Asp Ala Leu Val Lys Leu Lys Lys Lys Lys Gly Ala
        35                  40                  45

Met Glu Glu Leu Glu Lys Ala Leu Ser Ser Pro Gly Gln Pro Ser Lys
    50                  55                  60

Cys Val Thr Ile Pro Arg Ser Leu Asp Gly Arg Leu Gln Val Ser His
65                  70                  75                  80

Arg Lys Gly Leu Pro His Val Ile Tyr Cys Arg Val Trp Arg Trp Pro
                85                  90                  95

Asp Leu Gln Ser His His Glu Leu Lys Pro Leu Asp Ile Cys Glu Phe
            100                 105                 110
```

```
Pro Phe Gly Ser Lys Gln Lys Glu Val Cys Ile Asn Pro Tyr His Tyr
        115                 120                 125

Lys Arg Val Glu Ser Pro Val Leu Pro Pro Val Leu Val Pro Arg His
130                 135                 140

Asn Glu Phe Asn Pro Gln His Ser Leu Leu Val Gln Phe Arg Asn Leu
145                 150                 155                 160

Ser His Asn Glu Pro His Met Pro Gln Asn Ala Thr Phe Pro His Ser
                165                 170                 175

Phe His Gln Pro Asn Asn Thr Pro Phe Pro Leu Ser Pro Asn Ser Pro
                180                 185                 190

Tyr Pro Pro Ser Pro Ala Ser Ser Thr Tyr Pro Asn Ser Pro Ala Ser
        195                 200                 205

Ser Gly Pro Gly Ser Pro Phe Gln Leu Pro Ala Asp Thr Pro Pro Pro
        210                 215                 220

Ala Tyr Met Pro Pro Asp Asp Gln Met Gly Gln Asp Pro Ser Gln Pro
225                 230                 235                 240

Met Asp Thr Ser Asn Asn Met Ile Pro Gln Ile Met Pro Ser Ile Ser
                245                 250                 255

Ser Arg Asp Val Gln Pro Val Ala Tyr Glu Glu Pro Lys His Trp Cys
                260                 265                 270

Ser Ile Val Tyr Tyr Glu Leu Asn Asn Arg Val Gly Glu Ala Phe His
        275                 280                 285

Ala Ser Ser Thr Arg Val Leu Val Asp Gly Phe Thr Asp Pro Ser Asn
290                 295                 300

Asn Lys Ser Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
                340                 345                 350

Ile Phe Val Gln Ser Arg Asn Cys Asn Phe His His Gly Phe His Pro
        355                 360                 365

Thr Thr Val Cys Lys Ile Pro Ser Ser Cys Ser Leu Lys Ile Phe Asn
370                 375                 380

Asn Gln Glu Phe Ala Gln Leu Leu Ala Gln Ser Val Asn His Gly Phe
385                 390                 395                 400

Glu Ala Val Tyr Glu Leu Thr Lys Met Cys Thr Ile Arg Met Ser Phe
                405                 410                 415

Val Lys Gly Trp Gly Ala Glu Tyr His Arg Gln Asp Val Thr Ser Thr
                420                 425                 430

Pro Cys Trp Ile Glu Ile His Leu His Gly Pro Leu Gln Trp Leu Asp
        435                 440                 445

Lys Val Leu Thr Gln Met Gly Ser Pro Leu Asn Pro Ile Ser Ser Val
450                 455                 460

Ser
465

<210> SEQ ID NO 53
<211> LENGTH: 2205
<212> TYPE: DNA
<213> ORGANISM: Homo sapiens

<400> SEQUENCE: 53
actcactata gggctcgagc ggccgcctgg gcaggtgctt aggacctgtg tatgacgttt      60
```

-continued

```
cacctgtgat ctgttctttc ggtagccact gactttgagt tacaggaagg tctccgaaga       120
tttgtgtcaa atgacgtcaa tggccagctt gttttctttt actagtccag cagtaaagcg       180
attgttgggc tggaaacaag gtgatgagga ggagaaatgg gcagaaaagg cagttgatgc       240
tttggtgaag aaactaaaaa agaaaaaggg tgccatggag gaactggaga aagccttgag       300
cagtccagga cagccgagta atgtgtcac tattcccaga tctttagatg gacgcctgca        360
ggtttctcac agaaaaggct tacccccatgt tatatattgt cgtgtttggc gctggccgga     420
tttgcagagt catcatgagc taaagccgtt ggatatttgt gaatttcctt ttggatctaa       480
gcaaaaagaa gtttgtatca acccatacca ctataagaga gtggagagtc cagtcttacc      540
tccagtatta gtgcctcgtc ataatgaatt caatccacaa cacagccttc tggttcagtt      600
taggaacctg agccacaatg aaccacacat gccacaaaat gccacgtttc cacattcttt      660
ccaccagccc aacaacactc ctttccccntt atctccaaac agcccttatc cccttctcc     720 tgctagcagc acatatccca actccccagc aagttctgga ccaggaagtc catttcagct     780
cccagctgat acgcctcctc ctgcctatat gccacctgat gatcagatgg gtcaagatcc      840
ttcccagcct atggatacaa gcaataatat gattcctcag attatgccca gtatatccag      900
cagggatgtt cagcctgttg cctatgaaga gcctaaacat tggtgttcaa tagtctacta      960
tgaattaaac aatcgtgttg agaagctttt tcatgcatct tctactcgtg tgttagtaga     1020
tggattcaca gatccttcaa ataacaaaag tagattctgc ttgggtttgt tgtcaaatgt    1080
taatcgtaat tcgacaattg aaaacactag gcgacatatt ggaaaaggtg ttcatctgta    1140
ctatgttggt ggagaggtgt atgcggaatg cctcagtgac agcagcatat ttgtacagag    1200
taggaactgc aactttcatc atggctttca tcccaccact gtctgtaaga ttcccagcag    1260
ctgcagcctc aaaattttta acaatcagga gtttgctcag cttctggctc aatctgtcaa    1320
ccatgggttt gaggcagtat atgagctcac caaaatgtgt accattcgga tgagttttgt     1380
caagggttgg ggagcagaat atcaccggca ggatgtaacc agcacccat gttggattga       1440 gattcatctt catgggcctc ttcagtggct ggataaagtc cttactcaga tgggctcccc    1500
tctgaacccc atatcttctg tttcataatg cagaagtatt cttttcaatt atattgttag   1560
tggacttgtt ttaattttag agaaactttg agtacagata ctgtgagctt acattgaaaa    1620
cagatattac agcttatttt tttctacata attgtgacca atacatttgt attttgtgat   1680
gaatctacat ttgtttgtat tcatgttcat gtgattaact cttagaagtg ttgtaaaaga   1740
tgcagagtaa gtattatgcc ccagttcaga aatttggcat tgatcttaaa ctggaacatg    1800
cttttacttt attgccctaa caattttta ttaaatttat ttgaaaatgc atcacatgat      1860
gaaaaattat agcttataag agggcatata cagtgaagag taagttttcc ctcctactct     1920
cgatcttcca gaagctgtac ttttaccagt ttctttgtcc caccaactta aaaaaaaaa     1980 gtacaattca ttgttttgca aaagtgtatg gtagggctt aaaagaaact ataaagtttt    2040
atttgaatga acactatgca ctgctgtaac tggtagtgtt cagtaaaagc aaaatgatag    2100
ttttctagat gacataaaat ttacatttaa tacagataag tgttcttcag tgtaatgtga    2160
cttcatgcta tatatctttt gtaagacatt tcctttttta aaaa                    2205
```

MAD-RELATED GENES IN THE HUMAN

This application claims the benefit of co-pending provisional application Ser. No. 60/015,823, filed Apr. 18, 1996.

The U.S. Government has a paid-up license in this invention and the right in limited circumstances to require the patent owner to license others on reasonable terms as provided for by the terms of grants (CA35494, CA43460, CA09243, CA51183, CA57208, CA57345, and CA62924) awarded by the National Institutes of Health.

BACKGROUND OF THE INVENTION

Neoplasia involves the clonal expansion of cells which can escape the inhibitory influences that normally limit cell growth. The revolution in cancer research that has occurred over the last decade has largely involved the discovery of genes which confer these inhibitory influences and the delineation of mutations of these genes in various tumour types. TGF-β is one of the cytokines that can inhibit epithelial cell growth, and has been extensively studied for over a decade (1–5). Resistance to TGF-β is common in human cancers of many types, emphasizing the importance of this secreted polypeptide to the neoplastic process (6). However, the mechanisms by which tumour cells become resistant to TGF-β are generally unknown.

Much has been learned about TGF-β, its receptors, and its physiologic effects. TGF-β is now known to be the prototype for a large and conserved family of related polypeptides which have diverse physiologic functions in organisms as disparate as Drosophila, C. elegans, and Homo sapiens. The TGF-β signal is initially received by a receptor complex containing the products of three different genes (TGF-β receptor types RI, RII, and RII). This signal is apparently mediated by the serine/threonine kinase activities of RI and RII. Though a small number of potential substrates for these receptor kinases have been identified (7–11) the biochemical pathways that are stimulated by these kinase activities are largely unknown. However, genes which appear to function downstream of these receptors, on the basis of genetic criteria, have been identified in Drosophila and C. elegans. Mutations of the C. elegans genes sma-2, sma-3, and sma-4 confer phenotypic abnormalities identical to those observed with mutants of a TGF-β-family receptor gene (daf-4) in this organism (12). Savage et al. have proposed the name "dwarfins" for the corresponding proteins, homologues of which have been identified in the human (12). Similarly, mutations in the Drosophila Mad gene result in phenotypes like those observed in strains with mutations of the TGF-β-like ligand dpp (13,14). The Mad and sma genes are highly related by sequence, suggesting they all function similarly as mediators of TGF-β-like signaling (13,14). The Mad and sma genes have no relationship to other known signaling molecules, and encode no motifs that provide clues to their biochemical function. It is likely, however, that the final arbiters of the growth inhibition conferred by TGF-β family members include the cyclin-dependent kinase inhibitors (15).

The importance of the TGF-β pathway to colorectal tumorigenesis has recently been highlighted by two observations. A subset of colorectal tumors has been shown to harbor inactivating mutations of the TGF-β RII gene (16, 17). This subset, accounting for about 15% of total colorectal cancers (18–20), comprises tumours with characteristic defects in mismatch repair (21), and the high frequency of TGF-β RII gene mutations in this tumour type results from a mutation-prone polyadenosine tract within the coding region of the gene. Though most other colorectal cancers have been shown to be resistant to the inhibitory effects of TGF-β (2,6), the cause of such insensitivity is unknown. Mutations of the TGF-β RII gene or of the cdk inhibitor genes p15, p16, and p21 are not generally found in these tumours (22,23), suggesting that the defects lie in the intermediates in the signaling pathway. This hypothesis recently received experimental support with the discovery of the DPC4 gene (24). DPC4 was identified through a positional cloning approach designed to identify a pancreatic tumour suppressor gene on chromosome 18q21. The DPC4 gene was found to be highly related to Mad and sma and genetic alterations which affected DPC4 were observed in over 50% of pancreatic cancers. Analogous studies of other human cancers, including those of the colon, revealed that DPC4 was genetically altered in only a minority of cases (25,26). There is a need in the art for identification of additional human genes homologous to DPC4 and its lower eukaryotic homologues (hereinafter referred to as the Mad gene family) which are involved in neoplastic processes.

SUMMARY OF THE INVENTION

It is an object of the invention to provide a cDNA of the human Smad2 gene.

It is another object of the invention to provide an isolated Smad2 human protein.

It is yet another object of the invention to provide a pair of primers for amplification of the Smad2 gene.

It is still another object of the invention to provide probe for detecting Smad2 coding sequences.

It is an object of the invention to provide a preparation of antibodies which specifically binds a human Smad2 protein.

It is another object of the invention to provide methods for screening test substances for the ability to suppress neoplasia.

It is still another object of the invention to provide an animal which carries in its genome a mutation in the Smad2 gene.

It is yet another object of the invention to provide methods to aid in diagnosing or prognosing neoplasias.

It is a further object of the invention to provide methods of supplying wild-type Smad2 gene function to a cell which has lost Smad2 gene function.

It is another object of the invention to provide methods of supplying wild-type Smad2 gene function to a cell which has altered Smad2 gene function.

It is still another object of the invention to provide a method of detecting neoplastic tissue.

It is a further object of the invention to provide a method for detecting genetic predisposition to cancer.

It is another object of the invention to provide a cDNA of a human Smad gene.

It is yet another object of the invention to provide an isolated human Smad protein.

These and other objects of the invention are provided by one or more of the embodiments disclosed below. In one embodiment, an isolated cDNA of the human Smad2 gene is provided.

In another embodiment of the invention an isolated human Smad2 protein is provided.

In yet another embodiment of the invention a pair of primers for amplifying Smad2 coding sequences is provided. The first primer of said pair comprises at least 12 contiguous nucleotides selected from SEQ ID NO:1 and the second primer of said pair comprises at least 12 contiguous nucleotides selected from the complement of SEQ ID NO:1.

In still another embodiment of the invention a probe for detecting Smad2 coding sequences is provided. The probe comprises an oligonucleotide consisting of at least 12 contiguous nucleotides selected from SEQ ID NO:1 or the complement thereof.

In another embodiment of the invention a preparation of antibodies is provided. The preparation of antibodies specifically binds human Smad2 protein. The antibodies are not substantially immunoreactive with other human proteins.

In one embodiment of the invention a method of screening test substances for the ability to suppress a neoplastically transformed phenotype is provided. A test substance is applied to a cell which carries a mutation in the Smad2 gene. The ability of the test substance to suppress the neoplastically transformed phenotype is then determined.

In another embodiment of the invention another method of screening test substances for the ability to suppress neoplastic growth is provided. A test substance is administered to an animal which carries a mutant Smad2 gene. The ability of the test substance to prevent or suppress the growth of tumors is then determined.

In still another embodiment of the invention an animal which carries in its genome a mutant Smad2 gene is provided.

In yet another embodiment of the invention an animal which has been genetically engineered to contain in its genome an insertion mutation which disrupts the Smad2 gene is provided.

In a further embodiment of the invention a method of aiding in the diagnosis or prognosis of a neoplastic tissue of a human is provided. Alteration of wild-type coding sequences of the Smad2 gene are detected in a tumor tissue isolated from a human. The alteration indicates neoplasia of the tissue.

In still another embodiment of the invention a method for supplying wild-type Smad2 gene function to a cell which has lost Smad2 function is provided. A wild-type Smad2 gene is introduced into a cell which has lost Smad2 gene function such that said wild-type gene is expressed in the cell.

In yet another embodiment of the invention a method of supplying wild-type Smad2 gene function to a cell which has altered Smad2 gene function by virtue of a mutation in the Smad2 gene is provided. A portion of a wild-type Smad2 gene is introduced into a cell which has lost Smad2 gene function such that the portion of the Smad2 gene is expressed in the cell. The portion of the Smad2 gene encodes a part of the protein which is required for non-neoplastic growth of the cell.

In a further embodiment of the invention another method for supplying wild-type Smad2 gene function to a cell which has altered Smad2 gene function by virtue of a mutation in the Smad2 gene is provided. Human wild-type Smad2 protein is applied to a cell which has lost the wild-type Smad2 gene function.

In another embodiment of the invention a method of detecting the presence of a neoplastic tissue in a human is provided. An alteration of a wild-type Smad2 coding sequence is detected in a body sample isolated from a human. The alteration indicates the presence of a neoplastic tissue in the human.

In yet another embodiment of the invention a method of detecting genetic predisposition to cancer in a human is provided. Germline alteration of the wild-type Smad2 gene coding sequences is detected in a human sample selected from the group consisting of blood and fetal tissue. The alteration indicates predisposition to cancer.

In another embodiment of the invention cDNAs of human Smad genes are provided. The cDNAs are selected from the group consisting of Smad1 (SEQ ID NO:9), Smad3 (SEQ ID NO:5), Smad5 (SEQ ID NO:7), and Smad6 (SEQ ID NO:3).

In a further embodiment of the invention isolated human Smad proteins are provided. The proteins are selected from the group consisting of Smad1 (SEQ ID NO:10), Smad3 (SEQ ID NO:6), Smad5 (SEQ ID NO:8), and Smad6 (SEQ ID NO:4).

These and other embodiments of the invention which are described in more detail below, provide the art with additional tools and weapons for detecting and fighting against cancers.

BRIEF DESCRIPTION OF THE DRAWINGS

FIG. 1 Mad family members. Sequences from the carboxyl-termini of proteins encoded by Mad-related genes identified in the human genome are compared. For Smad6, the homology identified by data-base searching was confined to Mad residues 249 to 344, and are therefore not shown in this figure. Blocks of significant homology between all 9 Mad homologues were identified using the MACAW multiple alignment software (v2.01) (41). Smad2, SEQ ID NO: 38; Smad1, SEQ ID NO:39; Smad6, SEQ ID NO: 40; and Smad3, SEQ ID NO:41. Amino acids in conserved blocks are capitalized and shaded based on the means of their pairwise score. The sequence listing provides the complete amino acid sequences of the Drosophila Mad (SEQ ID NO:11), and *C. elegans* sma4 (SEQ ID NO:12), sma3 (SEQ ID NO:13), sma2 (SEQ ID NO:14) proteins and the human DPC4 (SEQ ID NO:15) protein.

FIG. 2 Sequence of Smad2. The predicted amino acid sequence determined from the studies described in the text is given for Smad2, (SEQ ID NO:42); and compared with that of Mad. The accession number for the Smad2 nucleotide sequence is U59911 (SEQ ID NO:51). No upstream stop codon was identified, so it is possible that the coding region initiates upstream of that indicated. The amino acid sequences were aligned using the MACAW (version 2.01) program. Blocks of significant homology were identified. Amino acids in conserved blocks are capitalized and shaded based on the mean of their pairwise score.

FIG. 3 Mutational analysis of Smad2. FIG. 3A illustrates the PCR analysis of genomic DNA from tumour Mx5 (lane 3), showing a homozygous deletion of Snad2. The PCR product shown is 110 bp, while the Smad5 PCR product (136 bp) served as a control. Lanes 1, 2, and 4 contained PCR products derived from other tumours. FIG. 3D shows the sequence of the deleted region in tumour Mx21 SEQ ID NOS:44 and 45, amino acid and nucleotide sequences of region without deletion; SEQ ID NOS:45 and 46, amino acid and nucleotide sequences in region with deletion.

FIG. 4. Amino acid alignment of human Smad5 (SEQ ID NO:48) & 6 (SEQ ID NO:49) with Drosophila Mad (SEQ ID NO:43). The coding regions of the novel human Smads are compared to the Drosophila prototype. Amino acids in conserved blocks are capitalized and shaded based on the means of their pairwise scores.

FIG. 5. Alignment of amino acids in the six known Smad genes. Conserved domains Wed DH1a, DH1b, DH2a, and DH2b) represent sequence blocks which were highly related in at least 5 of the 6 proteins. Dark blue vertical bands within blocks reflect identical residues in at least 5 genes. Thin horizontal black lines represent gaps introduced to optimize the alignment. Domains DH1 and DH2 as previously defined (12), were each divided into an 'a' and 'b' block to maintain the optimum sequence alignment, yielding 4 highly conserved sequence blocks. Using Smad1 as reference, DH1a, DH1b, DH2a, and DH2b extended from codons 20 to 45, 68 to 145, 265 to 367, and 402 to 454, respectively. The accession numbers for the human genes include corrections to previous database entries made on the basis of sequencing cDNA clones in our laboratory. Accession numbers for murine Smad genes (full-length for murine Smad1, 2 & 5 and partial for murine Smad3, 4 & 6) are provided in the last column. The chromosomal positions shown in the second column are derived from reference 3.

FIG. 6. Examples of mutation screening. FIG. 6A shows PCR products from cDNA of 8 breast cancer samples. Lanes marked "+" and "−" represent cDNA synthesis reactions with and without reverse transcriptase, respectively. The arrow points to the full length PCR product, which includes the entire open reading frame and a T7 promotor for the IVSP assay. FIG. 6B shows polypeptides translated from the PCR products in A were separated by electrophoresis through an SDS polyacrylamide gel. Full length proteins (marked with an arrow) were observed as the major bands in each case. The minor bands represent internally initiated polypeptides generated during in vitro translation.

DETAILED DESCRIPTION OF THE PREFERRED EMBODIMENTS

Figure 3B:
FIG. 3B demonstrates the in vitro synthesis of protein (IVSP) analysis of tumour Mx21 (lane 5), showing a slightly smaller Smad2 polypeptide than found normally. The normal size product migrating at approximately 50 kd was found in the other tumours analyzed (lanes 1–4, 6).

It is a discovery of the present inventors that five previously undescribed genes which are Mad-related exist in the human genome. The genes have been dubbed Smad1, Smad2, Snad3, Smad5, and Smad6. These genes are involved in the signaling pathway which mediates the effects of binding of TGF-β or TGF-β-like ligands to their receptors. Defects in these genes may lead to resistance to the inhibitory effects of TGF-β. Such resistance has been demonstrated in tumors of many types. Mutations have been found in Smad2 and Smad4 (DPC4) alleles in tumors. Thus, Smad2 and Smad4 are important genes for tumor suppression.

Moreover, three of these genes (Smad3, Smad5, and Smad6) have been localized to chromosomes noted to be frequently lost in human cancers. Chromosome 5q is often lost in lung and esophagus tumours, for example, but no relevant suppressor gene mutations have yet been identified, despite extensive study (31–34). Similarly, a recent report suggests that chromosome 15q losses are remarkably common in metastatic cancers of the breast, colon, and lung (35). The minimally lost regions (MLRs) in these cancers have been mapped to 5q31 and 15q14–21, close to the positions of the Smad3, Smad5, and Smad6 genes (See Table 1, below).

Human SmadcDNA molecules (SEQ ID NOS:1, 3, 5, 7, and 9), according to the present invention, are provided in isolated form, free from other sequences. They are identified by the chromosome and band position to which they have been mapped by fluorescence in situ hybridization, as well as by the determined sequences of the 5' and 3' ends. In addition, the amino acid sequences of the encoded proteins are provided (SEQ ID NOS:2, 4, 6, 8, and 10). This information unambiguously identifies the cDNAs which are provided. The cDNA molecules can be isolated from libraries of human cDNAs, from YACs, or from any other source of human cDNA. The cDNA molecules can be inserted into vectors, as is known in the art for various uses. The cDNA molecules can be linked to other sequences, such as selectable markers for certain uses. The CDNA molecules can have transcription and/or translation signals appended to either end, as is known in the art for expression of the encoded protein or for expression of anti-sense RNA molecules. Sequences from these cDNA molecules may be used, inter alia, to make hybridization probes and primers for PCR-based assays which may in turn be used to identify additional MAD-related genes involved in TGF-β signaling and/or in tumorigenesis.

The encoded proteins of the disclosed genes can be obtained by in vitro synthesis, or by synthesis in a recombinant organism or cell. Alternatively, the encoded proteins can be purified from cells or tissues naturally producing the proteins using antibodies made to the encoded proteins, or to peptide portions thereof. Isolated proteins need not be homogeneous to be useful, but can be partially purified (i.e., 10%, 50%, 75%, 90%, or 95% pure) from other cellular components and/or other proteins. The proteins may be used, inter alia, to generate anti-Smad antibodies or to supply a wild-type Smad protein function to cells which have lost that function. Wild-type Smad proteins may also be compared with Smad proteins in tissue samples in order to detect the presence of altered Smad proteins.

Antibodies according to the present invention bind specifically to human Smad proteins and thus are not substantially immunoreactive with other human proteins. Specific binding, as used herein, means that the antibody binds with higher affinity to a Smad protein than to non-Smad protein. No substantial immunoreactivity, as used herein, means that the antibody does not bind with high affinity to a non-Smad protein. Under standard conditions, antibodies that bind specifically to human Smad proteins do not cross-react with other proteins, as evidenced by Western blotting. Anti-Smad antibodies can be raised by immunization of mammals with peptide portions of the encoded proteins, either alone or attached to another protein to render it more immunogenic. Alternatively, the entire protein can be used as an immunogen. Antiserum can be used directly or after some purification steps to render it more specific. The immunized animals can also be used to raise monoclonal antibodies, as is known in the art, through the process of fusion of antibody producing cells to myeloma cells. Any techniques known in the art for raising polyclonal or monoclonal antibodies can be used. The antibodies are useful for purifying Smad proteins and for detecting alterations in Smad proteins which result from mutations in Smad genes.

Primer pairs are typically used for amplification of the cDNAs. Particularly suitable primers are disclosed below, but any primers can be used which comprise oligonucleotides of at least 10, 12, or 14 contiguous nucleotides. Each of the primers in a pair is complementary to an opposite strand of the gene. Typically at least 15, 18, or 20 contiguous nucleotides are desirable. In some circumstances it may be desirable that additional moieties be attached to the contiguous nucleotides of the gene. For example, restriction enzyme sites may be desirable to facilitate cloning. Transcription and translation signals may be desirable to facilitate in vitro assays of RNA and protein products (e.g., IVSP).

Similarly, nucleotide probes can be useful for identifying the disclosed genes in clinical test samples. Probes can be similarly sized to primers, but can often be much larger, up to the size of the full cDNA. Fluorescent or radioactive labels may be optionally appended to the probes to facilitate recognition.

Mutations in the Smad2 gene lead to neoplasia; thus cells harboring mutations in this gene can be used to screen for candidate therapeutic agents. The mutation may occur spontaneously in test cells or may be induced by mutagenic methods. In a preferred embodiment, the cells are genetically engineered to contain the mutation. By applying a candidate test substance to such cells and observing its effect, one can determine whether such an agent suppresses the transformed phenotype of the cell. The test substance may be a pharmacologic agent already known in the art or may be a substance previously unknown to have any pharmacologic activity. The substance may be naturally occurring or may be designed in the laboratory. It may be isolated from a microorganism, plant, or animal or may be produced recombinantly or synthetically by chemical methods known in the art. Any phenotype of the cell which is indicative of neoplastic transformation can be observed. Such phenotypes are well known in the art. Cells to be used are preferably epithelial cells, but any type of cell which exhibits a transformed phenotype and carries a mutation in the Smad2 gene can be used. Suitable methods for culturing cells, such as monolayer or explant culture methods, are well known in the art. Similar assays can be performed using whole animals which carry a mutant Smad2 gene as disclosed. The test substance may be administered to the animal orally or by injection. The ability of a candidate test substance to suppress or prevent the growth of tumors provides an indication of usefulness as a therapeutic agent.

The present invention also provides animals which carry a mutation in the Smad2 gene. The animals are made using techniques which are well known in the art. The mutation may be a missense mutation, an insertion, a deletion, or a rearrangement. These animals can be used to screen for potential therapeutic agents and to study the initiation, progression, or stimulation of neoplasia, for example by exposure to potential environmental carcinogenic agents. Diagnosis and/or prognosis of neoplasia can be aided using the Smad2 gene of the present invention. The presence of a mutation in the Smad2 gene can be used to aid in diagnosing a cancer or in prognosing a clinical outcome. Mutations can be detected by assaying a Smad2 allele, mRNA, or protein. Presence of a deviation from the wild-type Smad2 sequence or from the Smad2 sequence found in the surrounding normal tissue indicates a mutation. Conventional assays for mutations as are known in the art can be used. For example, sequence analysis, Southern, Northern, or Western analysis, can be used. Immunoblotting, immunohistochemistry, and other immunological techniques can be used and are routinely practiced in the art. Alternatively, Smad2 gene sequences in the samples may be amplified using, inter alia, PCR. Mutations in the sequence can then be detected using mutation- or wild-type-specific nucleic acid probes. Samples for testing for mutations or mutant gene products can be a suspected or confirmed neoplastic tissue, or a body sample, such as serum, stool, urine, or sputum. Germline mutations can also be detected, for example, by testing blood or fetal tissue.

Replacement therapy can be used to remedy a defective gene. This can be accomplished by introducing all or a portion of a wild-type Smad2 gene into a cell which has lost responsiveness to TGF-β by virtue of a mutation in the Smad2 gene. The portion of the Snad2 gene includes at least the portion comprising codon 345–358 of SEQ ID NO:1 or a portion comprising at least 30 nucleotides which include the mutated codons. Any vectors known in the art can be used to introduce the gene or gene portion, including, but not limited to retroviral or adenoviral vectors. Other techniques such as liposome-mediated gene transfer can be used as well. The gene or gene portion can be introduced on a vector which remains extrachromosomal, such as a minichromosome or episome. It may be introduced into cells which have been removed from the body or by direct injection into suitable target organs or tumors. Alternatively, the gene or gene portion may be introduced so that it integrates in the genome. In an alternative embodiment a wild-type Smad2 protein having the sequence shown in SEQ ID NO:2 can be applied to cells which have a mutation in the Smad2 gene. The protein can be applied in a suitable vehicle for internalization within cells, such as liposomes. Targeting of the agents to particular organs or tissues can be accomplished as is known in the art, using specific targeting moieties, such as antibodies, receptors, or ligands.

The following examples are provided for exemplification purposes only and are not intended to limit the scope of the invention.

EXAMPLE 1

This example demonstrates the identification of Mad homologues.

To identify human homologues of Mad, we searched expressed-sequence tag (EST) databases. These databases contain a significant fraction of the total human genes (27), and have been previously shown to be valuable cancer gene discovery tools (28). Several sequences were used as search queries, including the Mad gene, sma genes, and Smad4. Once candidate homologues were identified, new searches were carried out with these in order to identify additional homologues or additional clones of the same genes. In toto, thirty EST clones were identified that contained statistically significant matches to the queries. Sequences of these clones were then aligned to connect clones into contigs. In some cases, clones were re-sequenced to resolve ambiguities in the EST entries. This approach allowed us to define portions of five different human genes, dubbed Smad2, Smad5, Smad3, Smad6, and Smad1. In four of the five genes, the homologies included the predicted carboxyl-termini of the gene products, and these are aligned in FIG. 1 along with other members of the Mad family. The highest conservation was noted with Smad1, which was predicted to have 58 of 59 (98%) carboxyl-terminal residues identical to that of the Mad gene product. Smad3 (85% identity) and Smad2 (83% identity) were also very similar to Mad, while Smad5 differed significantly (29% identity). In comparison, Smad4 was only 47% identical to Mad in this region and was not more highly related to Smad5 than to the other genes.

We next determined the chromosome localizations of these genes. Despite their sequence similarities, we were eventually able to design primers and conditions that specifically amplified each gene from human DNA and did not amplify related genes from the mouse or hamster genomes (Table 1). These primers were used to screen a somatic cell hybrid panel, affording localization of Smad2, Smad5, Smad3, Smad6, and Smad1 to chromosomes 18, 15, 15, 5, and 4, respectively. The same PCR conditions were then used to screen a YAC panel. This was successful in four cases, and the YAC's were used to further localize Smad2, Smad5, Smad3, Smad6 to chromosomes 18q21, 15q15–21, 15q15–21, and 5q31, respectively. One YAC was found to contain both Shad5 and Smad3, indicating that these genes were within approximately 1 Mb. These data are summarized in Table 1.

EXAMPLE 2

This example demonstrates the detailed analysis of Smad2.

The localization of Smad2 to chromosome 18q21 was particularly intriguing in light of previous studies of this chromosomal region in colorectal cancers. In particular, it

TABLE 1

Mapping Information for Mad-related genes

| NAME | LOCATION | ACCESSION NUMBERS | MAPPING PRIMERS | PCR PRODUCT | CEPH YAC |
|---|---|---|---|---|---|
| Smad2 | 18q21 | U59911[a] (SEQ ID NO:51) | F-gtccatcttgccattcacg-3' (SEQ ID NO:16) | 194 bp | y739a3 |
|  |  |  | R-tggtgatggctttctcaagc-3' (SEQ ID NO:17) |  |  |
| Smad5 | 15q21 | U59913[a] (SEQ ID NO:53) | F-tggacaaaacaagaaagacgc-3' (SEQ ID NO:18) | 161 bp | y750g9 |
|  |  |  | R-caaaaaccatacaccaaaccc-3' (SEQ ID NO:19) |  |  |
| Smad3 | 15q21 |  | F-tgggctccccaagcatccg-3' (SEQ ID NO:20) | 136 bp | y750g9 |
|  |  |  | R-ttccttgacaacaatgggttg-3' (SEQ ID NO:21) |  |  |
| Smad6 | 5q31 |  | F-taaacattggtgttcaatagtc-3' (SEQ ID NO:22) | 174 bp | y759d5 |
|  |  |  | R-tgttttcaattgtcgaattacg-3' (SEQ ID NO:23) |  |  |
| Smad1 | Chrom. 4[b] |  | F-tcaatcgtgtctgactcatcc-3' (SEQ ID NO:24) | 215 bp | not found |
|  |  |  | R-gagcagaataccaccgcc-3' (SEQ ID NO:25) |  |  |

[a]sequence determined in this study. In all cases except Smad2, only sequences at the 5' or 3' ends were determined.
[b]reference 42.

Methods

Identification of Mad homologues. Full length protein sequences of Mad and its known homologues were used to search the National Center for Biotechnology Information (NCBI) expressed sequence tag database (dbest) using the 'tblastn' search program (36). New matches were used for subsequent rounds of searching and to create contigs. To confirm sequence information at the 3' ends of the newly identified genes, manual sequencing of cDNA clones obtained from the IMAGE consortium (37) was performed, and the resultant sequences recorded through the Accession Numbers listed in Table 1.

Chromosome localization. PCR primers were designed to amplify the genes identified in the data-base search. A variety of primers were synthesized for each gene, searching for pairs which would provide robust signals of the expected length from human DNA but would not amplify hamster or mouse DNA. Appropriate primer pairs (see Table 1) were then used for amplification of DNA from a somatic cell hybrid panel containing isolated human chromosomes (Coriell Institute for Medical Research, Camden, N.J.). The same primers were then used to screen the CEPH A YAC panel (Research Genetics, Atlanta, Ga.). The chromosomal positions of the identified YACs were determined from published genetic maps (38).

has been shown that over 60% of such cancers lose genetic information from this chromosomal region (29). The minimally lost region (MLR) encompasses a 16 Mb interval between marker D18S535 and D18S858 and includes Smad4 (25). To determine the position of Smad2 with respect to this region, we studied somatic cell hybrids containing portions of chromosome 18q, YAC libraries, and colorectal cancer cell lines with homozygous deletions in the area (25, 30). These studies revealed that Smad2 was between D18S535 and Smad4, approximately 3 Mb from each. No YAC clone was identified which contained both Smad4 and Smad2.

Thus both Smad2 and Smad4 were located within the MLR and were candidates for the presumptive tumour suppressor gene(s) located in this region. There is much precedent for clustering of genes of similar function, thought to arise through gene duplication of an ancestral precursor. As a prelude to a mutational analysis, we therefore determined the complete coding sequence of Smad2 and compared it to that of Smad4 and other Mad homologues. The predicted amino acid sequence of Smad2 (SEQ ID NO:42) is shown in FIG. 2, and the nucleotide sequence entered in Genbank under Accession #U599 11 (SEQ ID NO:51). Smad2 encoded a 467 residue open reading frame, with maximal homology to other Mad family members at the amino- and carboxyl-termini of the protein. Smad2 was more similar to Mad (62% identity over 373 aa) than to the C. elegans homologues sma-2 (50% identify over 365 aa), sma-3 (45% identity over 204 aa), sma-4 (25% identify over 361 aa) or to Smad4 (44% over 158 aa).

We then evaluated Smad2 in a panel of 18 early-passage colorectal cancer lines, each containing an allelic loss of the MLR on chromosome 18q. RT-PCR was performed on RNA from these xenografts, using primers which did not amplify the Smad2 mouse homologue. Smad2 was found to be expressed in the normal colon mucosa, normal brain, and in 17 of the 18 colorectal tumours. In the one case (Mx5) in which Smad2 was not expressed at detectable levels, a homozygous deletion of Smad2 sequences was identified (FIG. 3A). This deletion was verified with three separate primer pairs and included both the 5' and 3' ends of Smad2, but did not extend proximally to D18S535 or distally to Smad4 (not shown). The deletion was not found in DNA from the normal colon of the corresponding patient, so represented a somatic alteration.

Figure 3C:
FIG. 3C shows a PCR analysis of DNA from tumour Smad2 (lane 2), showing a deletion of 42 bp in tumour Mx21 not found in the DNA from normal colon of the same patient (lane 1) or in the cDNA (lane 3) or genomic DNA (lane 4) of other non-neoplastic samples.

To search for alterations of Smad2 that would alter the size of the encoded polypeptide, an in vitro synthesized protein assay was performed by incorporating recognition signals for in vitro transcription and translation in the primers used for RT-PCR. One tumour, Mx21, exhibited a smaller protein in this assay (FIG. 3B). The alteration was traced to a 42 bp deletion, extending from codon 345 to 358 (FIG. 3C and FIG. 3D). PCR amplification of normal genomic DNA across regions flanking the deletions demonstrated that it occurred completely within an exon (rather than representing a deleted exon). The deletion was somatic, as it was not found in the patient's normal cells (FIG. 3c). In addition, the deleted residues were highly conserved, with thirteen of the fourteen residues identical to the homologous region in the Mad gene.

Finally, we attempted to search for missense mutations of Smad2 by direct sequencing of RT-PCR products in the 16 tumours encoding an apparently full-length polypeptide. No mutations or polymorphisms were detected within the entire open reading frame in any of the tumours.

Methods

Sequence and Mutational Analysis of Smad2

Sequences already entered into the data-bank (Table 1), representing the 5' and 3' ends of Smad2, were used to design primers for amplification of cDNA via RT-PCR. Direct sequencing of the RT-PCR products allowed us to determine the entire coding sequence and correct ambiguities in the previous EST entries. The new sequence, including the entire ORF, has been recorded under Accession Number U59911. RT-PCR products were transcribed and translated in vitro as described (39). The entire coding region of the gene was amplified using primers 5'-GGA TCC TAA TAC GAC TCA CTA TAG GGA GAC CAC CAT GGG TAA GAA CAT GTC GTC CAT C-3' (SEQ ID NO:26) (including signals for transcription and translation) and 5'-TTT CCA TGG GAC TTG ATT GG-3' (SEQ ID NO:27). Sequencing of the RT-PCR products was performed using internal primers, available from the authors upon request, end-labeled with $^{32}$P-γ-ATP and SequiTherm Polymerase (Epicentre, Madison, Wis.), as described (40).

EXAMPLE 3

This example demonstrates the comparison of Smad genes.

Partial sequences for known Smad genes were used to make hybridization probes and primers for PCR-based assays. Hybridization probes were used to screen cDNA libraries using standard methods. Clones were manually sequenced using $^3$P-labelled terminator chemistry (ThermoSequenase, Amersham Life Science, Cleveland, Ohio). Contigs of the clones were used to create a full length coding sequence. The coding region of each gene, including portions originally derived from expressed sequence tags found by computer searches (National Center for Biotechnology Information, World Wide Web page), was confirmed or corrected by manual sequencing as described above. To determine the 5' end of Smand5, the rapid amplification of cDNA ends technique was employed, using primers derived from the cDNA sequence obtained by cDNA cloning.

The amino acid sequence of the six known Smads were aligned using Macaw Version 2.0.3 optimizing for the mean pairwise score. Blocks of homology shown in FIG. 5 were produced by selecting all permissible and statistically significant blocks as determined by Macaw. Conserved domains in FIG. 5 were identified by selecting sequence that had a more stringent selection, including mean pairwise scores above 80 in at least five of the six genes.

Sequence for two novel human Smad genes (Smad5 and Smad6; FIG. 4) were determined through a combination of database searching, cDNA library screening, and PCR-based techniques. These sequences were compared to the published sequences of Smad1–4 (in the case of Smad3, corrections to the published sequence were made on the basis of independently cloning and sequencing the entire gene). Alignment of the six genes documented four highly conserved domains (D)H's, indicated by boxes in FIG. 3), with 125 residues identical in at least five of the genes (indicated by vertical blue lines in the boxes). The naming of these domains was based on a previous comparison of three C. elegans Mad genes and a Drosophila Mad gene that showed two major regions of homology; corresponding to DH1 and DH2. Our comparison of the six human genes show that further division of the two original domains yields a significantly better alignment. The structure of all six human genes was very similar, though Smad6 lacked DH1. Evidence that Smad6 was full length included a reasonable translation initiation consensus sequence at the presumed initiating methionine and an upstream stop codon.

EXAMPLE 4

This example demonstrates mutations in the Smad genes.

Mutation Detection. The in vitro protein synthesis assay (IVSP) was used in combination with manual sequencing. Each Smad studied was amplified with PCR primers that spanned the entire coding region. All forward primers listed below were synthesized with the following T7 promoter sequence at the 5' end: 5'-gga tcc taa tac gac tca cta tag gga g-3' (nucleotides 1–25 of SEQ ID NO:26). The T7 promotor and the Kozak consensus sequences shown for each forward primer allowed in vitro transcription and translation. The following gene specific primers were used: Smad1F=5'-T7-acc acc atg gea cca tat cca agg agt ata act ag (SEQ ID NO:28); Smad1R=5'-ttt m ata tga atc caa cag ttg gtc aca gag g (SEQ ID NO:29); Smad2F=acc acc atg ggt a aga aca tgt cgt cc atc (SEQ ID NO:30); Smad2R=ttt cca tgg gac ttg att gg (SEQ ID NO:31); Smad3F=gag cca gcc atg tcg tcc atc c (SEQ ID NO:32); Smad3R=ttt tcc cca agc ctg ccc tc (SEQ ID NO:33); Smad5F=5'-acc acc atg gtc tcc gaa gat ttg tgt caa (SEQ ID NO:34); Smad5R=5'-tttm ata tct gtt ttc aat gta agc tca cag (SEQ ID NO:35); Smad6F=5' acc acc atg gaa tct ccg cca cct ccc tac (SEQ ID NO:36); Smad6R=5'-cg cca cta tct ggg gtt g (SEQ ID NO:37). PCR products were transcribed and translated in vitro, and the resultant proteins separated by SDS-polyacrylamide gel electrophoresis, as described . The RT-PCR products were also used for sequencing with internal primers (primer sequences available upon request).

Mutations of Smad2 and Smad4 have been observed in human tumors (24, 25, 43–46), but the other four genes have not previously been evaluated for genetic alterations. To address this issue, a panel of 167 cancer cell lines (passaged in vitro or as xenografts in nude mice) was assembled for mutation analysis. Cell lines rather than primary tumors were chosen so that nucleic acids from non-neoplastic cells within primary tumor specimens would not cloud interpretation. The panel included cancers of the following types: cancers of the colorectum (70), breast (22), brain (22), lung (15), pancreas (12), head and neck (8), ovary (6), esophagus (4), stomach (4), and prostate (4). These cancers represent most of the common tumor types, and several have been shown to lose heterozygosity at chromosomal positions encompassing the Smad genes.

RNA from each of the 167 lines was used as template in reverse transcriptase-polymerase chain reactions (RT-PCR), using primer sequences specific for Smad1, 2, 3, 5, and 6. These genes were ubiquitously expressed, as revealed by expression of each of the four genes at easily detectable levels in 165 of the 167 samples (examples in FIG. 6). To screen for mutations, we employed an in vitro synthesized protein (IVSP) assay. RT-PCR products containing the open reading frame of each of the four genes were transcribed and translated in vitro, and the resultant polypeptides separated by SDS-acrylamide gel electrophoresis. Full length products were observed in each of the 165 samples yielding RT-PCR products, and no truncated proteins were observed.

The RT-PCR and IVSP assays detect most types of mutations affecting potential tumor suppressor genes, such as homozygous deletions, nonsense mutations, deletions or insertions creating frameshifts, and splice site mutations. A small number of missense mutations have been identified in the DH2 domains of Smad2 and Smad4 (24, 25, 44–46), that would have been missed by an IVSP assay. In order to detect missense mutations that occurred at significant frequency, we chose 50 tumors from our panel for sequencing of the DH2a and HD2b domains. DH2b domains in the four other Smads. The RT-PCR products were manually sequenced from the same amplified cDNA used for the IVSP assay. Only the wild-type sequence was identified in each case.

In summary, the four genes analyzed here, plus the previously analyzed Smad2 and Smad4, are expressed in virtually all cancers analyzed, suggesting they are important for signal transduction in most cell types. Mutations of these genes in tumors, however, are not widespread. Smad 4 is altered in a significant fraction of pancreatic cancers and in a minority of colorectal tumors, but rarely in other tumor types, but rarely in other tumor types and Smad 2 is altered only in a small fraction of colorectal and lung tumors but in no other common tumor types. The other four genes do not appear to be frequently mutated in any of the cancer types analyzed here, and mutations of the TGF-( receptors themselves are also uncommon except in the subset of colorectal cancers with mismatch repair deficiency (16, 17). Thus the basis of TGF-β resistance in human cancers is unlikely to be due, in general, to alterations of currently known genes. Assuming that the TGF-β resistance in tumors has a genetic basis, other components of the TGF-β signaling pathway, such as the one recently identified in *Xenopus laevis* must be responsible.

Three additional genes, apparently not identical to those disclosed here, have been previously described (12). Though the number of Mad-related human genes may appear large, this number should be viewed in the context of other genes involved in TGF-β-like signaling. Over 20 TGF-β family members have been described in humans, including several bone morphogenetic proteins and activins, each with its own tissue distribution and function (3). Three genes encode the receptor complex that mediates signaling by TGF-β1, β2, and β3, and other genes encode receptors for additional ligands in the TGF-β superfamily. The large number of Mad-related genes may therefore parallel the large number of receptors and ligands which initiate signaling. It is possible that each receptor-ligand combination is associated with a unique Mad family member complex. Alternatively, as sma-2, sma-3, and sma-4 mutations yield identical phenotypes in *C. elegans,* Savage et al. have suggested that the encoded proteins are likely to either form a heteromeric complex or be activated sequentially, in a signaling cascade (12). In view of the high conservation of this family of genes, the human homologues may function in a similar manner.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Attisano, L., Wrana, J. L., Lopez-Casillas, F. & Massague, J. TGF-beta receptors and actions. *Biochim. Biophys. Acta* 1222, 71–80 (1994).
2. Brattain, M. G., Howell, G., Sun, L. Z. & Willson, J. K. Growth factor balance and tumor progression. *Curr. Opin. Oncol.* 6, 77–81 (1994).
3. Kingsley, D. M. The TGF-beta superfamily: new members, new receptors, and new genetic tests of function in different organisms. *Genes Dev.* 8, 133–146 (1994).
4. Roberts, A. B. & Sporn, M. B. Physiological actions and clinical applications of transforming growth factor-beta (TGF-beta). *Growth Factors* 8, 1–9 (1993).

5. Satterwhite, D. J. & Moses, H. L. Mechanisms of transforming growth factor-beta 1-induced cell cycle arrest. *Invasion Metastasis* 14, 309–318 (1994).
6. Fynan, T. M. & Reiss, M. Resistance to inhibition of cell growth by transforming growth factor-beta and its role in oncogenesis. *Crit. Rev. Oncog.* 4, 493–540 (1993).
7. Chen, R. H., Miettinen, P. J., Maruoka, E. M., Choy, L. & Derynck, R. A WD-domain protein that is associated with and phosphorylated by the type II TGF-beta receptor. Nature 377, 548–552 (1995).
8. Wang, T., Donahoe, P. K. & Zervos, A. S. Specific interaction of type I receptors of the TGF-beta family with the immunophilin FKBP-12. *Science* 265, 674–6 (1994).
9. Atfi, A., Lepage, K., Allard, P., Chapdelaine, A. & Chevalier, S. Activation Of a Serine Threonine Kinase Signaling Pathway By Transforming Growth Factor Type Beta. *Proc. Natl. Acad. Sci.* 92, 12110–12114 (1995).
10. Yamaguchi, K., et al. Identification Of a Member Of the Mapkkk Family As a Potential Mediator Of Tgf-Beta Signal Transduction. *Science* 270, 2008–2011 (1995).
10 11. Wang, T. W., et al. The P21(Ras) Farnesyltransferase Alpha Subunit In TGF-Beta and Activin Signaling. *Science* 271, 1120–1122 (1996).
12. Savage, C., et al. Caenorhabditis Elegans Genes Sma2, Sma-3, and Sma-4 Define a Conserved Family Of Transforming Growth Factor Beta Pathway Components. *Proc. Natl. Acad. Sci.* USA 93, 790–794 (1996).
13. Sekelsky, J. J., Newfeld, S. J., Raftery, L. A., Chartoff, E. H. & Gelbart, W. M. Genetic characterization and cloning of mothers against dpp, a gene required for decapentaplegic function in Drosophila melanogaster. *Genetics* 139, 1347–1358 (1995).
14. Hursh, D. A., Padgett, R. W. & Gelbart, W. M. Cross regulation of decapentaplegic and Ultrabithorax transcription in the embryonic visceral mesoderm of Drosophila. *Development* 117, 1211–1222 (1993).
15. Massague, J. & Polyak, K. Mammalian antiproliferative signals and their targets. *Curr. Opin. Genet. Dev.* 5, 91–6 (1995).
16. Markowitz, S., et al. Inactivation of the type II TGF-beta receptor in colon cancer cells with microsatellite instability. *Science* 268, 1336–1338 (1995).
17. Parsons, R., et al. Microsatellite Instability and Mutations Of the Transforming Growth Factor Beta Type II Receptor Gene In Colorectal Cancer. *Cancer Res.* 55, 5548–5550 (1995).
18. Ionov, Y., Peinado, M. A., Malkhosyan, S., Shibata, D. & Perucho, M. Ubiquitous somatic mutations in simple repeated sequences reveal a new mechanism for colonic carcinogenesis. *Nature* 363, 558–561 (1993).
19. Thibodeau, S. N., Bren, G. & Schaid, D. Microsateffite instability in cancer of the proximal colon. *Science* 260, 816–9 (1993).
20. Aaltonen, L. A., et al. Clues to the pathogenesis of familial colorectal cancer. *Science* 260, 812–816 (1993).
21. Marra, G. & Boland, C. R. Hereditary nonpolyposis colorectal cancer: the syndrome, the genes, and historical perspectives. *J. Natl. Cancer Inst.* 87, 1114–25 (1995).
22. Jen, J., et al. Deletion of p16 and p15 genes in brain tumors. *Cancer Res.* 54, 6353–6358 (1994).
23. Shiohara, M., et al. Absence of WAF1 mutations in a variety of human malignancies. *Blood* 84, 3781–4 (1994).
24. Hahn, S. A., et al. Dpc4, A Candidate Tumor Suppressor Gene At Human Chromosome 18q21.1. *Science* 271, 350–353 (1996).
25. Thiagalingam, S. Evaluation of Chromosome 18q in Colorectal Cancers. submitted (1996).
26. Schutte, M. Tissue-restriction in DPC4 gene alterations. submitted (1996).
27. Korenberg, J. R., Chen, X. N., Adams, M. D. & Venter, J. C. Toward a cDNA Map Of the Human Genome. *Genomics* 29, 364–370 (1995).
28. Papadopoulos, N., et al. Mutation of a mutL homolog in hereditary colon cancer. *Science* 263, 1625–1629 (1994).
29. Fearon, E. R. & Vogelstein, B. A genetic model for colorectal tumorigenesis. *Cell* 61, 759–67 (1990).
30. Rojas, K., Silverman, G. A., Hudson, J. R., Jr. & Overhauser, J. Integration of the 1993–94 Genethon genetic linkage map for chromosome 18 with the physical map using a somatic cell hybrid mapping panel. *Genomics* 25, 329–330 (1995).
31. Shibagaki, I., et al. Allelotype analysis of esophageal squamous cell carcinoma. *Cancer Res.* 54, 2996–3000 (1994).
32. Aoki, T., et al. Allelotype study of esophageal carcinoma. *Genes Chrom. Cancer* 10, 177–82 (1994).
33. Ogasawara, S., et al. Common Deleted Region On the Long Arm Of Chromosome 5 In Esophageal Carcinoma. *Gastroenterology* 110, 52–57 (1996).
34. Wieland, I., et al. Allelic Deletion Mapping On Chromosome 5 In Human Lung Carcinomas. *Oncogene* 12, 97–102 (1996).
35. Wick, W. Evidence for a novel tumor suppressor gene on chromosome 15 associated with progression to a metastatic stage in breast cancer. *Oncogene* 12, 973–978 (1996).
36. Altschul, S. F., Gish, W., Miller, W., Myers, E. W. & Lipman, D. J. Basic local alignment search tool. *J. Mol. Biol.* 215, 403–10 (1990).
37. Hillier, L. Generation and preliminary analysis of over 200,000 human expressed sequence tags. Nature, in press (1996).
38. Hudson, T. J., et al. An STS-Based Map Of the Human Genome. *Science* 270, 1945–1954 (1995).
39. Powell, S. M., et al. Molecular diagnosis of familial adenomatous polyposis. *N. Engl. J. Med.* 329, 1982–1987 (1993).
40. Leach, F. S., et al. Mutations of a mutS homolog in hereditary nonpolyposis colorectal cancer. *Cell* 75, 1215–1225 (1993).
41. Schuler, G. D., Altschul, S. F. & Lipman, D. J. A workbench for multiple alignment construction and analysis. Proteins 9, 180–190 (1991).
42. Houlgatte, R., et al. The genexpress index—A resource for gene discovery and the genic map of the human genome. *Genome Research* 5, 272–304 (1995).
43. Riggins, G. J., Kinzler, K. W., Vogelstein, B., and Thiagalingam, S., Mad-related genes in the human. *Nature Genetics* 13: 347–349 (1996).
44. Uchida, K., Nagatake, M., Osada, H., Yatabe, Y., Kondo, M., Mitsudomi, T., Masuda, A., Takahashi, T., and Takahashi, T. Somatic in vivo alterations of the WV18-1 Gene at 18q21 in human lung cancers, *Cancer Research* 56: 5583–5585 (1996).
45. Nagatake, M., Takagi, Y., Osada, H., Uchida, K., Misudomi, T., Saji, S., Shimokata, K., T ahash, T., and Takahash, T. Somatic in vivo alterations of the DPC4 gene at 19821 in human lung cancers, *Cancer Research* 56: 2718–2720 (1996).
46. Eppert, K., Scherer, S. W., Ozcelik, H., Pirone, R., Hoodless, P., Kim, H., Tsui, L.- C., Bapat, B., Gallinger, S., Andrulis, I. L., Thomsen, G. H., Wrana, L., and Attisano, L. MADR2 maps to 18q21 and encodes a TGF-beta-regulated MAD-related protein that is mutated in colorectal carcinoma. *Cell* 86: 543–552 (19916).

What is claimed is:

1. An isolated cDNA of a human Smad5 gene which encodes a Smad5 protein having the amino acid sequence of GenBank Accession No. U59913 (SEQ ID NO:52).

2. The isolated cDNA of claim 1 which has the coding sequence of GenBank Accession No. U59913 (SEQ ID NO:53).

3. An isolated cDNA of a human Smad5 gene which has a coding sequence of nucleotides 375 to 1769 of SEQ ID NO:7.

* * * * *